(12) United States Patent
Ko

(10) Patent No.: US 8,324,175 B2
(45) Date of Patent: *Dec. 4, 2012

(54) COMPOSITIONS AND METHODS FOR THE TREATMENT OF CANCER

(76) Inventor: Young Hee Ko, Owings Mills, MD (US)

( * ) Notice: Subject to any disclaimer, the term of this patent is extended or adjusted under 35 U.S.C. 154(b) by 149 days.

This patent is subject to a terminal disclaimer.

(21) Appl. No.: 12/849,682

(22) Filed: Aug. 3, 2010

(65) Prior Publication Data

US 2011/0008418 A1 Jan. 13, 2011

Related U.S. Application Data

(63) Continuation-in-part of application No. 12/697,169, filed on Jan. 29, 2010, now Pat. No. 8,022,042, which is a continuation-in-part of application No. 11/706,868, filed on Feb. 14, 2007, now Pat. No. 7,754,693.

(60) Provisional application No. 61/148,385, filed on Jan. 29, 2009, provisional application No. 60/773,653, filed on Feb. 16, 2006.

(51) Int. Cl.
| | |
|---|---|
| A61K 31/194 | (2006.01) |
| A61K 31/7088 | (2006.01) |
| A61K 31/375 | (2006.01) |
| A61K 38/16 | (2006.01) |
| A61K 9/27 | (2006.01) |
| A61K 39/00 | (2006.01) |
| A61K 39/395 | (2006.01) |
| A61K 38/44 | (2006.01) |

(52) U.S. Cl. ............ 514/23; 514/25; 514/193; 514/474; 514/557; 424/94.4; 424/130.1; 424/725; 424/769

(58) Field of Classification Search .................... 514/23, 514/25, 193, 474, 557; 424/94.4, 130.1, 424/725, 769
See application file for complete search history.

(56) References Cited

U.S. PATENT DOCUMENTS

| | | | |
|---|---|---|---|
| 4,536,387 A | 8/1985 | Sakamoto et al. | |
| 5,759,547 A | 6/1998 | Maione | |
| 5,759,837 A | 6/1998 | Kuhajda et al. | |
| 5,854,067 A | 12/1998 | Newgard et al. | |
| 5,891,717 A | 4/1999 | Newgard et al. | |
| 6,031,000 A | 2/2000 | Nissen et al. | |
| 6,284,786 B1 | 9/2001 | Casciari et al. | |
| 6,312,662 B1 | 11/2001 | Erion et al. | |
| 6,448,030 B1 | 9/2002 | Rust et al. | |
| 6,670,330 B1 | 12/2003 | Lampidis et al. | |
| 7,338,940 B2 | 3/2008 | Lampidis et al. | |
| 7,754,693 B2 * | 7/2010 | Ko ................................. | 514/23 |
| 8,022,042 B2 * | 9/2011 | Ko ................................. | 514/23 |
| 2001/0046997 A1 | 11/2001 | Abraham et al. | |
| 2002/0006915 A1 | 1/2002 | Strong et al. | |
| 2002/0068711 A1 | 6/2002 | Pedersen et al. | |
| 2003/0018166 A1 | 1/2003 | Sacchettini et al. | |
| 2003/0087961 A1 | 5/2003 | Ko et al. | |
| 2003/0139331 A1 | 7/2003 | Martin et al. | |
| 2004/0029826 A1 | 2/2004 | Sokoloff et al. | |
| 2004/0126789 A1 | 7/2004 | Park et al. | |
| 2004/0167079 A1 | 8/2004 | Tidmarsh | |
| 2004/0167196 A1 | 8/2004 | Tidmarsh | |
| 2006/0058383 A1 | 3/2006 | Huang et al. | |
| 2006/0154867 A1 | 7/2006 | Sokoloff et al. | |
| 2006/0172953 A1 | 8/2006 | Tidmarsh et al. | |
| 2009/0326068 A1 | 12/2009 | Ko et al. | |

FOREIGN PATENT DOCUMENTS

| | | |
|---|---|---|
| WO | WO 2006/020403 | 2/2006 |
| WO | WO 2007/097989 | 8/2007 |
| WO | WO 2008-076964 | 6/2008 |

OTHER PUBLICATIONS

U.S. Appl. 12/697,169, filed Jan. 29, 2010; Young Hee Ko; Notice of Allowance issued May 20, 2011.

Kerr et al; Phase I Clinical DNA Pharmacokinetic Study of Leucovorin and Infusional Hepatic Arterial Fluorouracil; Journal of Clinical Oncology; Dec. 1995; vol. 13, No. 12; p. 2968-2972.

(Continued)

*Primary Examiner* — Raymond Henley, III
(74) *Attorney, Agent, or Firm* — Thorpe North & Western LLP

(57) ABSTRACT

The present invention discloses anti-cancer compositions, and associated methods, including an anti-cancer composition comprising: a cellular energy inhibitor having the structure according to formula I

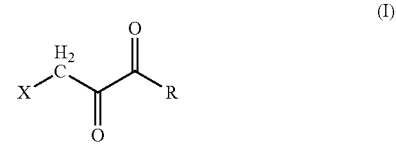

(I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R'", C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R'", R" represents H, C1-C6 alkyl, or C6-C12 aryl, and R'" represents H, C1-C20 alkyl or C6-C12 aryl. The anti-cancer composition can additionally comprise at least one sugar, which stabilizes the cellular energy inhibitor by substantially preventing the inhibitor from hydrolyzing. Also, the anti-cancer composition can comprise a hexokinase inhibitor. Further, the anti-cancer composition can comprise a biological buffer that is present in an amount sufficient to at least partially deacidify the cellular energy inhibitor and neutralize metabolic by-products of the cellular energy inhibitor.

32 Claims, 11 Drawing Sheets

OTHER PUBLICATIONS

Lin et al.; Effects of 90Y-Microsphers on Liver Tumors: Comparison of Intratumoral Injection Method and Inta-Arterial Injection Method; Nov. 2000; The Journal of Nuclear Medicine; vol. 41, No. 11; p. 1892-1897.
Arafat et al.; Toxicities Related to Intraarterial Infusions of Cisplatin and Etoposide in Patients with Brain Tumors; Journal of Neurooncology; 1999; vol. 42 pp. 73-77.
Bar et al.; Sorbitol Removal by the Metastatic Liver: A Predictor of Systemic Toxicity of Intra-Arterial Chemotherapy in Patients with Liver Metastases; 1999; Journal of Hepatology; vol. 30; pp. 1112-1118.
Geshwind et al.; Novel Therapy for Liver Cancer: Direct Intraarterial Injection of a Potent Inhibitor of ATP Production; Jul. 15, 2002; Cancer Research; vol. 62; p. 3909-3913.
Gobin et al.; Intraarterial Chemotherapy for Brain Tumors by Using a Spatial Dose Fractionation Algorithm and Pulsatile Delivery; Mar. 2001; Radiology; vol. 218 No. 3; p. 724-732.
Ko et al.; Glucose Catabolism in the Rabbit VX2 Tumor Model for Liver Cancer: Characterization and Targeting Hexokinase; 2001; Cancer Letters; vol. 173; pp. 83-91.
Kostron et al.; Photodynamic Treatment of Malignant Brain Tumors; Sep. 28, 1990; Jg 102, Heft 18: 531-535; (Abstract Only).
Mathupala et al.; Glucose Catabolism in Cancer Cells, Identification and Characteriszation of a Marked Activation Response of the Type II Hexokinase Gene to Hypoxic Conditions; Nov. 16, 2001; vol. 276, No. 46; pp. 43407-43412.
Pedersen et al.; Mitochondrial Bound Type II Hexokinase: A Key Player in the Growth and Survival of Many Cancers and an Ideal Prospect for Therapeutic Intervention; Biochimica et Biophysica Acta; 2002; vol. 1555 pp. 14-20.
Soulen et al.; Intraarterial Chemotherapy with Limb-Sparing Resection of Large Soft-Tissue Sarcomas of the Extremities; JFIR; Nov. 1992; vol. 3; 659-663.
Wang et al.; Isolated Lower Extremity Chemotherapeutic Infusion for Treatment of Osteosarcoma: Experimental Study and Preliminary Clinical Report; J. Vasc. Interv. Radiol.; Jun. 2001; vol. 12; pp. 731-737.
Johns Hopkins Medical Institutions Office Of Communications and Public Affairs; Energy Blocker may be Potential Liver Cancer Treatment; www.hopkinsmedicine.org/press/2002/July/020715.htm.
Ko et al.; Alkylation of Isocitrate Lyase from *Escherichia coli* by 3-Bromopyruvate; May 1, 1990; Archives of Biochemistry and Biophysics; vol. 278, No. 2; pp. 373-380.
Oya et al.; Evaluation of Experimental Liver Tumors Using Fluorine-18-2-Fluoro-2-Deoxy-D-Glucose PET; J. Nuci. Med.; Dec. 1993; vol. 34, No. 12; pp. 2124-2129.
Arora et al.; Functional Significance of Mitochondrial Bound Hexinase in Tumor Cell Metabolism, Evidence for Preferential Phosphorylation of Glucose by Intramitochondrially Generated ATP; The Journal of Biological Biochemistry; Nov. 25, 1988; vol. 263, No. 33; p. 17422-17428.
Mathupala et al.; Glucose Catabolism in Cancer Cells, Isolation, Sequence, and Activity of the Promoter for Type II Hexokinase; The Journal of Biological Chemistry; Jul. 14, 1995; vol. 270, No. 28; pp. 16918-16925.
Rempel et al.; Glucose Catabolism in Cancer Cells: Amplification of the Gene Encoding Type II Hexokinase; Cancer Research; Jun. 1, 1996; vol. 56, pp. 2468-2471.
Parry et al.; Intracellular Localization and Properties of Particulate Hexokinase in the Novikoff Ascites Tumor, Evidence for an Outer Mitochondrial Membrane Location; The Journal of Biological Chemistry; Sep. 25, 1983; vol. 258, No. 18; pp. 10904-10912.
Bustamante et al.; Energy Metabolism of Tumor Cells, Requirement for a Form of Hexokinase with a Propensity for Mitochondrial Binding; The Journal of Biological Chemistry; Aug. 25, 1981; vol. 256, No. 16; pp. 8699-8704.
Weinhouse; Glycolysis, Respiration, and Anomalous Gene Expression in Experimental Hepatomas: G.H.A. Clowes Memorial Lecture; Cancer Research; Oct. 1972; vol. 32, No. 10; pp. 2007-2016.
Sharma et al.; Structure of Isocitrate Lyase, A Persistence Factor of *Mycobacterium tuberculosis*; Nature Structural Biology; Aug. 2000; vol. 7 No. 8; pp. 663-668.
Chen et al.; The Warburg Effect and its Cancer Therapeutic Implications; Journal of Bioenergestics and Bioenergestic and Biomembranes; 2007; vol. 39, No. 3; pp. 267-274.
Pelicano et al.; Glycolysis Inhibition for Anticancer Treatment; Oncogene; 2005; vol. 25; pp. 4633-4646.
Ihrlund et al.; 3-Bromopyruvate as Inhibitor of Tumor Cell Energy Metabolism and Chemopotentiator of Platinum Drugs; Molecular Oncology; Jun. 2008; vol. 2, No. 1; p. 94-101.
Kang et al.; 2-Deoxyglucose: An Anticancer and Antiviral Therapeutic, But Not Any More a Low Glucose Mimetic; Life Sciences; Feb. 2006; vol. 78, No. 12; pp. 1392-1399.
PCT Application PCT/US2010/022664; filed Jan. 29, 2010; Young Hee Ko; ISR mailed Oct. 28, 2010.
Pedersen; Tumor Mitoichondria and the Bioenergetics of Cancer Cells; Prog. Exp. Tumor Res.; 1978; vol. 22; p. 190-274.
Fiebig et al.; Relevance of tumor models for Anticancer Drug Development; 1999; Contrib. Oncol. Basel. Karger; vol. 54; pp. 109-120.
Ko et al.; Advanced Cancers: Eradication in all cases using 3-Bromopyruvate Therapy to Deplete ATP; 2004; Biochemical and Biophysical Research Communications; vol. 324; pp. 269-275.
Pederson, P., "Energy Blocker" Kills Big Tumors in Rats; Audio File-Johns Hopkins Medicine, Office of Corporate Communications; Oct. 14, 2004.
Ko et al.; Advanced Cancers: Eradication in All Cases Using 3-Bromopyruvate Therapy to Deplete ATP; Press Release, BBRC Supporting Online Material; Nov. 5, 2004.
PCT Application PCT/US2011/046475; filed Aug. 3, 2011; Young Hee Ko; International Search Report mailed Mar. 23, 2012.
Vossen, et al.; "Development of a new orthotopic animal model of metastalic liver cancer in the rabbit CX2 model: effect on metastases after partial hepatectomy, intra-arterial treatment with 3-bromopyruvate and chemoembolization"; Reachsearch Paper;Clin Exp Metastasis /20/) 25;811-817; DOI 10.1007/S10585-008-9195-X; Received Apr. 2, 2008/Accepted: Jul. 10, 2008; Springer Science+Business Media B.V. 2008.
Pathania; et al.; "Opportunities in discovery and delivery of anticancer drugs targetingmitochondria and cancer cell metabolism"; Advanced Drug Delivery Review 61 (2009) 1250-1275.

* cited by examiner

```
            10         20         30         40         50         60
     MIAAQLLAYY FTELKDDQVK KIDKYLYAMR LSDETLIDIM TRFRKEMKNG LSRDFNPTAT
            70         80         90        100        110        120
     VKMLPTFVRS IPDGSEKGDF IALDLGGSSF RILRVQVNHE KNQNVHMESE VYDTPENIVH
           130        140        150        160        170        180
     GSGSQLFDHV AECLGDFMEK RKIKDKKLPV GFTFSFPCQQ SKIDEAILIT WTKRFKASGV
           190        200        210        220        230        240
     EGADVVKLLN KAIKKRGDYD ANIVAVVNDT VGTMMTCGYD DQHCEVGLII GTGTNACYME
           250        260        270        280        290        300
     ELRHIDLVEG DEGRMCINTE WGAFGDDGSL EDIRTEFDRE IDRGSLNPGK QLFEKMVSGM
           310        320        330        340        350        360
     YLGELVRLIL VKMAKEGLLF EGRITPELLT RGKFNTSDVS AIEKNKEGLH NAKEILTRLG
           370        380        390        400        410        420
     VEPSDDDCVS VQHVCTIVSF RSANLVAATL GAILNRLRDN KGTPRLRTTV GVDGSLYKTH
           430        440        450        460        470        480
     PQYSRRFHKT LRRLVPDSDV RFLLSESGSG KGAAMVTAVA YRLAEQHRQI EETLAHFHLT
           490        500        510        520        530        540
     KDMLLEVKKR MRAEMELGLR KQTHNNAVVK MLPSFVRRTP DGTENGDFLA LDLGGTNFRV
           550        560        570        580        590        600
     LLVKIRSGKK RTVEMHNKIY AIPIEIMQGT GEELFDHIVS CISDFLDYMG IKGPRMPLGF
           610        620        630        640        650        660
     TFSFPCQQTS LDAGILITWT KGFKATDCVG HDVVTLLRDA IKRREEFDLD VVAVVNDTVG
           670        680        690        700        710        720
     TMMTCAYEEP TCEVGLIVGT GSNACYMEEM KNVEMVEGDQ GQMCINMEWG AFGDNGCLDD 730        740        750        760        770        780
     IRTHYDRLVD EYSLNAGKQR YEKMISGMYL GEIVRNILID FTKKGFLFRG QISETLKTRG
           790        800        810        820        830        840
     IFETKFLSQI ESDRLALLQV RAILQQLGLN STCDDSILVK TVCGVVSRRA AQLCGAGMAA
           850        860        870        880        890        900
     VVDKIRENRG LDRLNVTVGV DGTLYKLHPH FSRIMHQTVK ELSPKCNVSF LLSEDGSGKG
           910
     AALITAVGVR LRTEASS
```

FIG. 10

```
         10         20         30         40         50         60
MDCEHSLSLP CRGAEAWEIG IDKYLYAMRL SDETLIDIMT RFRKEMKNGL SRDFNPTATV
         70         80         90        100        110        120
KMLPTFVRSI PDGSEKGDFI ALDLGGSSFR ILRVQVNHEK NQNVHMESEV YDTPENIVHG
        130        140        150        160        170        180
SGSQLFDHVA ECLGDFMEKR KIKDKKLPVG FTFSFPCQQS KIDEAILITW TKRFKASGVE
        190        200        210        220        230        240
GADVVKLLNK AIKKRGDYDA NIVAVVNDTV GTMMTCGYDD QHCEVGLIIG TGTNACYMEE
        250        260        270        280        290        300
LRHIDLVEGD EGRMCINTEW GAFGDDGSLE DIRTEFDREI DRGSLNPGKQ LFEKMVSGMY
        310        320        330        340        350        360
LGELVRLILV KMAKEGLLFE GRITPELLTR GKFNTSDVSA IEKNKEGLHN AKEILTRLGV
        370        380        390        400        410        420
EPSDDDCVSV QHVCTIVSFR SANLVAATLG AILNRLRDNK GTPRLRTTVG VDGSLYKTHP
        430        440        450        460        470        480
QYSRRFHKTL RRLVPDSDVR FLLSESGSGK GAAMVTAVAY RLAEQHRQIE ETLAHFHLTK
        490        500        510        520        530        540
DMLLEVKKRM RAEMELGLRK QTHNNAVVKM LPSFVRRTPD GTENGDFLAL DLGGTNFRVL
        550        560        570        580        590        600
LVKIRSGKKR TVEMHNKIYA IPIEIMQGTG EELFDHIVSC ISDFLDYMGI KGPRMPLGFT
        610        620        630        640        650        660
FSFPCQQTSL DAGILITWTK GFKATDCVGH DVVTLLRDAI KRREEFDLDV VAVVNDTVGT 670        680        690        700        710        720
MMTCAYEEPT CEVGLIVGTG SNACYMEEMK NVEMVEGDQG QMCINMEWGA FGDNGCLDDI
        730        740        750        760        770        780
RTHYDRLVDE YSLNAGKQRY EKMISGMYLG EIVRNILIDF TKKGFLFRGQ ISETLKTRGI
        790        800        810        820        830        840
FETKFLSQIE SDRLALLQVR AILQQLGLNS TCDDSILVKT VCGVVSRRAA QLCGAGMAAV
        850        860        870        880        890        900
VDKIRENRGL DRLNVTVGVD GTLYKLHPHF SRIMHQTVKE LSPKCNVSFL LSEDGSGKGA
        910
ALITAVGVRL RTEASS
```

FIG. 11

```
            10         20         30         40         50         60
    MGQICQRESA TAAEKPKLHL LAESEIDKYL YAMRLSDETL IDIMTRFRKE MKNGLSRDFN
            70         80         90        100        110        120
    PTATVKMLPT FVRSIPDGSE KGDFIALDLG GSSFRILRVQ VNHEKNQNVH MESEVYDTPE
           130        140        150        160        170        180
    NIVHGSGSQL FDHVAECLGD FMEKRKIKDK KLPVGFTFSF PCQQSKIDEA ILITWTKRFK
           190        200        210        220        230        240
    ASGVEGADVV KLLNKAIKKR GDYDANIVAV VNDTVGTMMT CGYDDQHCEV GLIIGTGTNA
           250        260        270        280        290        300
    CYMEELRHID LVEGDEGRMC INTEWGAFGD DGSLEDIRTE FDREIDRGSL NPGKQLFEKM
           310        320        330        340        350        360
    VSGMYLGELV RLILVKMAKE GLLFEGRITP ELLTRGKFNT SDVSAIEKNK EGLHNAKEIL
           370        380        390        400        410        420
    TRLGVEPSDD DCVSVQHVCT IVSFRSANLV AATLGAILNR LRDNKGTPRL RTTVGVDGSL
           430        440        450        460        470        480
    YKTHPQYSRR FHKTLRRLVP DSDVRFLLSE SGSGKGAAMV TAVAYRLAEQ HRQIEETLAH
           490        500        510        520        530        540
    FHLTKDMLLE VKKRMRAEME LGLRKQTHNN AVVKMLPSFV RRTPDGTENG DFLALDLGGT
           550        560        570        580        590        600
    NFRVLLVKIR SGKKRTVEMH NKIYAIPIEI MQGTGEELFD HIVSCISDFL DYMGIKGPRM
           610        620        630        640        650        660
    PLGFTFSFPC QQTSLDAGIL ITWTKGFKAT DCVGHDVVTL LRDAIKRREE FDLDVVAVVN
           670        680        690        700        710        720
    DTVGTMMTCA YEEPTCEVGL IVGTGSNACY MEEMKNVEMV EGDQGQMCIN MEWGAFGDNG
           730        740        750        760        770        780
    CLDDIRTHYD RLVDEYSLNA GKQRYEKMIS GMYLGEIVRN ILIDFTKKGF LFRGQISETL
           790        800        810        820        830        840
    KTRGIFETKF LSQIESDRLA LLQVRAILQQ LGLNSTCDDS ILVKTVCGVV SRRAAQLCGA
           850        860        870        880        890        900
    GMAAVVDKIR ENRGLDRLNV TVGVDGTLYK LHPHFSRIMH QTVKELSPKC NVSFLLSEDG
           910        920
    SGKGAALITA VGVRLRTEAS S
```

FIG. 12

```
         10         20         30         40         50         60
MAKRALRDFI DKYLYAMRLS DETLIDIMTR FRKEMKNGLS RDFNPTATVK MLPTFVRSIP
         70         80         90        100        110        120
DGSEKGDFIA LDLGGSSFRI LRVQVNHEKN QNVHMESEVY DTPENIVHGS GSQLFDHVAE
        130        140        150        160        170        180
CLGDFMEKRK IKDKKLPVGF TFSFPCQQSK IDEAILITWT KRFKASGVEG ADVVKLLNKA
        190        200        210        220        230        240
IKKRGDYDAN IVAVVNDTVG TMMTCGYDDQ HCEVGLIIGT GTNACYMEEL RHIDLVEGDE
        250        260        270        280        290        300
GRMCINTEWG AFGDDGSLED IRTEFDREID RGSLNPGKQL FEKMVSGMYL GELVRLILVK
        310        320        330        340        350        360
MAKEGLLFEG RITPELLTRG KFNTSDVSAI EKNKEGLHNA KEILTRLGVE PSDDDCVSVQ
        370        380        390        400        410        420
HVCTIVSFRS ANLVAATLGA ILNRLRDNKG TPRLRTTVGV DGSLYKTHPQ YSRRFHKTLR
        430        440        450        460        470        480
RLVPDSDVRF LLSESGSGKG AAMVTAVAYR LAEQHRQIEE TLAHFHLTKD MLLEVKKRMR
        490        500        510        520        530        540
AEMELGLRKQ THNNAVVKML PSFVRRTPDG TENGDFLALD LGGTNFRVLL VKIRSGKKRT
        550        560        570        580        590        600
VEMHNKIYAI PIEIMQGTGE ELFDHIVSCI SDFLDYMGIK GPRMPLGFTF SFPCQQTSLD 610        620        630        640        650        660
AGILITWTKG FKATDCVGHD VVTLLRDAIK RREEFDLDVV AVVNDTVGTM MTCAYEEPTC
        670        680        690        700        710        720
EVGLIVGTGS NACYMEEMKN VEMVEGDQGQ MCINMEWGAF GDNGCLDDIR THYDRLVDEY
        730        740        750        760        770        780
SLNAGKQRYE KMISGMYLGE IVRNILIDFT KKGFLFRGQI SETLKTRGIF ETKFLSQIES
        790        800        810        820        830        840
DRLALLQVRA ILQQLGLNST CDDSILVKTV CGVVSRRAAQ LCGAGMAAVV DKIRENRGLD
        850        860        870        880        890        900
RLNVTVGVDG TLYKLHPHFS RIMHQTVKEL SPKCNVSFLL SEDGSGKGAA LITAVGVRLR

TEASS
```

FIG. 13

```
            10         20         30         40         50         60
    MIASHLLAYF FTELNHDQVQ KVDQYLYHMR LSDETLLEIS KRFRKEMEKG LGATTHPTAA
            70         80         90        100        110        120
    VKMLPTFVRS TPDGTEHGEF LALDLGGTNF RVLWVKVTDN GLQKVEMENQ IYAIPEDIMR
           130        140        150        160        170        180
    GSGTQLFDHI AECLANFMDK LQIKDKKLPL GFTFSFPCHQ TKLDESFLVS WTKGFKSSGV
           190        200        210        220        230        240
    EGRDVVALIR KAIQRRGDFD IDIVAVVNDT VGTMMTCGYD DHNCEIGLIV GTGSNACYME
           250        260        270        280        290        300
    EMRHIDMVEG DEGRMCINME WGAFGDDGSL NDIRTEFDQE IDMGSLNPGK QLFEKMISGM
           310        320        330        340        350        360
    YMGELVRLIL VKMAKEELLF GGKLSPELLN TGRFETKDIS DIEGEKDGIR KAREVLMRLG
           370        380        390        400        410        420
    LDPTQEDCVA THRICQIVST RSASLCAATL AAVLQRIKEN KGEERLRSTI GVDGSVYKKH
           430        440        450        460        470        480
    PHFAKRLHKT VRRLVPGCDV RFLRSEDGSG KGAAMVTAVA YRLADQHRAR QKTLEHLQLS
           490        500        510        520        530        540
    HDQLLEVKRR MKVEMERGLS KETHASAPVK MLPTYVCATP DGTEKGDFLA LDLGGTNFRV
           550        560        570        580        590        600
    LLVRVRNGKW GGVEMHNKIY AIPQEVMHGT GDELFDHIVQ CIADFLEYMG MKGVSLPLGF
           610        620        630        640        650        660
    TFSFPCQQNS LDESILLKWT KGFKASGCEG EDVVTLLKEA IHRREEFDLD VVAVVNDTVG
           670        680        690        700        710        720
    TMMTCGFEDP HCEVGLIVGT GSNACYMEEM RNVELVEGEE GRMCVNMEWG AFGDNGCLDD
           730        740        750        760        770        780
    FRTEFDVAVD ELSLNPGKQR FEKMISGMYL GEIVRNILID FTKRGLLFRG RISERLKTRG
           790        800        810        820        830        840
    IFETKFLSQI ESDCLALLQV RAILQHLGLE STCDDSIIVK EVCTVVARRA AQLCGAGMAA
           850        860        870        880        890        900
    VVDRIRENRG LDALKVTVGV DGTLYKLHPH FAKVMHETVK DLAPKCDVSF LQSEDGSGKG
           910
    AALITAVACR IREAGQR
```

FIG. 14

COMPOSITIONS AND METHODS FOR THE TREATMENT OF CANCER

CROSS-REFERENCE TO RELATED APPLICATIONS AND CLAIM OF PRIORITY

This application is a continuation-in-part of U.S. patent application Ser. No. 12/697,169 filed on Jan. 29, 2010, now U.S. Pat. No. 8,022,042, which is a continuation-in-part of U.S. patent application Ser. No. 11/706,868 filed on Feb. 14, 2007, now U.S. Pat. No. 7,754,693. Application Ser. No. 12/697,169 claims the benefit of U.S. provisional patent application Ser. No. 61/148,385 filed on Jan. 29, 2009, and application Ser. No. 11/706,868 claims the benefit of U.S. provisional patent application Ser. No. 60/773,653 filed on Feb. 16, 2006. All of the above are incorporated herein by reference in their entireties.

This application incorporates-by-reference the sequence listing material found in the ASCII text entitled 337006.txt, which file was created Aug. 31, 2010 and has a file size of 39.9 kb.

BACKGROUND

Each year, hundreds of thousands of men, women, and children in the United States are afflicted with some form of cancer. Worldwide, millions die of cancers including those of the bone, bladder, blood (leukemias), brain, breast, colon, cervix, esophagus, intestine, kidney, liver, lung, mouth, nose, nerves, ovaries, pancreas, prostate, skin, stomach, testis, throat, thyroid, uterus, and vagina.

Over the years, a number of methods have been used to treat cancer including radiation and chemotherapy. The primary goal of these treatments is to kill all the cancer cells. However, many healthy cells are invariably destroyed in a race to kill the cancer cells before the treatment(s) kill the patient. Even today, the more measured and quantitative uses of radiation and chemotherapy can cause illness and even death in some patients. At the same time, in some types of cancer, the malignant cells remain difficult to treat.

Consequently, ongoing research and developmental efforts continue in the medicinal arts involving the treatment of various cancers.

SUMMARY

It has been recognized by the present inventor that it would be advantageous to develop an anti-cancer composition that is effective over an array of cancers, that is safe for use in humans, and that avoids or at least minimizes adverse drug experiences associated with traditional cancer treatments.

Briefly, and in general terms, the invention is directed to an anti-cancer composition comprising: a cellular energy inhibitor having the structure according to formula I

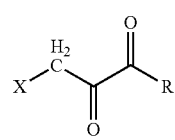

(I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl. Additionally, the anti-cancer composition can comprise at least one sugar, which stabilizes the cellular energy inhibitor by substantially preventing the inhibitor from hydrolyzing. The anti-cancer composition can further comprise a hexokinase inhibitor. Further, the anti-cancer composition can also comprise a biological buffer that is present in an amount sufficient to at least partially deacidify the cellular energy inhibitor and neutralize metabolic by-products of the cellular energy inhibitor. The anti-cancer composition can further comprise a glycolysis inhibitor.

In one embodiment, a method for the treatment of cancer can comprise administering to a subject any of the anti-cancer compositions described herein in a therapeutically effective amount.

In another embodiment, a method of minimizing toxicity of a cellular energy inhibitor of formula (I) to a subject receiving the cellular energy inhibitor can comprise combining in the subject, the cellular energy inhibitor with a biological buffer that is present in an amount sufficient to at least partially deacidify the cellular energy inhibitor and neutralize metabolic by-products of the cellular energy inhibitor due to its chemical reaction and/or cellular metabolism.

In yet another embodiment, a method of minimizing an adverse drug experience associated with administration of any of the anti-cancer compositions as described herein to a subject can comprise administering the anti-cancer composition to the subject at a time when the subject's blood insulin/glucagon ratio is in the range of about 1 to about 10.

In still another embodiment, a method for assessing killing efficacy of any of the anti-cancer compositions described herein in a subject can comprise measuring a lactic acid level in the subject prior to administration of the anti-cancer composition; administering the anti-cancer composition to the subject; measuring the lactic acid level in the subject after administration of the anti-cancer composition; and determining the killing efficacy by measuring and/or correlating the difference between the lactic acid levels as a function of treatment time.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 10 is an amino acid sequence of hexokinase 1 (isoform 1) in accordance with an embodiment of the present invention;

FIG. 11 is an amino acid sequence of hexokinase 1 (isoform 2) in accordance with an embodiment of the present invention;

FIG. 12 is an amino acid sequence of hexokinase 1 (isoform 3) in accordance with an embodiment of the present invention;

FIG. 13 is an amino acid sequence of hexokinase 1 (isoform 4) in accordance with an embodiment of the present invention; and FIG. 14 is an amino acid sequence of hexokinase 2 in accordance with an embodiment of the present invention.

Figure 1:
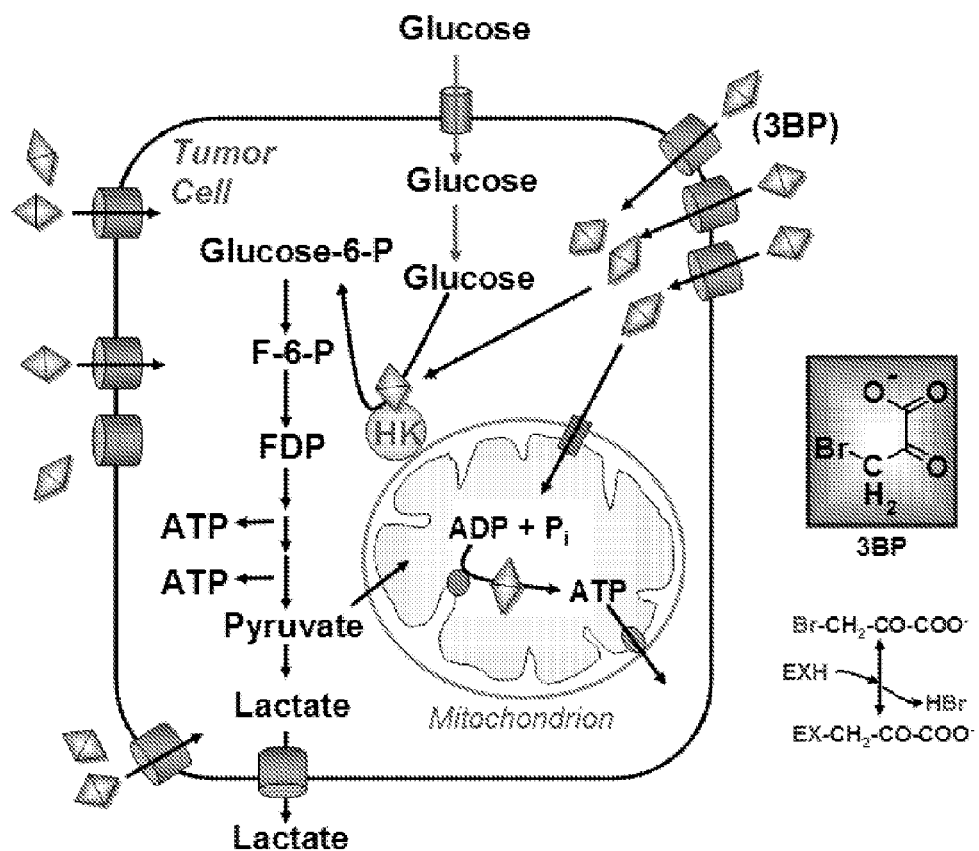
FIG. 1 is a schematic of a cancer cell energy production in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Before the present invention is disclosed and described, it is to be understood that this disclosure is not limited to the particular process steps and materials disclosed herein because such process steps and materials may vary somewhat. It is also to be understood that the terminology used herein is used for the purpose of describing particular embodiments only. The terms are not intended to be limiting because the scope of the present disclosure is intended to be limited only by the appended claims and equivalents thereof.

It must be noted that, as used in this specification and the appended claims, the singular forms "a," "an," and "the" include plural referents unless the context clearly dictates otherwise.

The composition of the present invention may include a pharmaceutically acceptable carrier, and other ingredients as dictated by the particular needs of the specific dosage formulation. Such ingredients are well known to those skilled in the art. See for example, Gennaro, A. *Remington: The Science and Practice of Pharmacy* 19$^{th}$ ed. (1995), which is incorporated by reference in its entirety.

As used herein, "administration," and "administering" refer to the manner in which a drug is presented to a subject. Administration can be accomplished by various art-known routes such as oral, alimentary, parenteral, transdermal, inhalation, implantation, etc. Thus, an oral administration can be achieved by drinking, swallowing, chewing, sucking of an oral dosage form comprising the drug. Parenteral administration can be achieved by injecting a drug composition intravenously, intra-arterially, intramuscularly, intrathecally, or subcutaneously, etc. Transdermal administration can be accomplished by applying, pasting, rolling, attaching, pouring, pressing, rubbing, etc., of a transdermal preparation onto a skin surface. These and additional methods of administration are well-known in the art.

As used herein, "non-oral administration" represents any method of administration in which a drug composition is not provided in a solid or liquid oral dosage form, wherein such solid or liquid oral dosage form is traditionally intended to substantially release and or deliver the drug in the gastrointestinal tract beyond the mouth and/or buccal cavity. Such solid dosage forms include conventional tablets, capsules, caplets, etc., which do not substantially release the drug in the mouth or in the oral cavity.

It is appreciated that many oral liquid dosage forms such as solutions, suspensions, emulsions, etc., and some oral solid dosage forms may release some of the drug in the mouth or in the oral cavity during the swallowing of these formulations. However, due to their very short transit time through the mouth and the oral cavities, the release of drug from these formulations in the mouth or the oral cavity is considered de minimus or insubstantial, unless otherwise indicated. Thus, buccal patches, adhesive films, sublingual tablets, and lozenges that are designed to release the drug in the mouth are non-oral compositions for the present purposes.

In addition, it is understood that the term "non-oral" includes parenteral, transdermal, inhalation, implant, and vaginal or rectal formulations and administrations. Further, implant formulations are to be included in the term "non-oral," regardless of the physical location of implantation. Particularly, implantation formulations are known which are specifically designed for implantation and retention in the gastrointestinal tract. Such implants are also considered to be non-oral delivery formulations, and therefore are encompassed by the term "non-oral."

As used herein, "subject" refers to a mammal that may benefit from the administration of a drug composition or method of this invention. Examples of subjects include humans, and other animals such as horses, pigs, cattle, sheep, goats, dogs (felines), cats (canines), rabbits, rodents, primates, and aquatic mammals. In one embodiment, subject can refer to a human.

As used herein, "effective amount" or "therapeutically effective amount," or similar terms, refers to a non-toxic but sufficient amount of a drug, to achieve therapeutic results in treating a condition for which the drug is known to be effective or has been found to be effective as disclosed herein. Various biological factors may affect the ability of a delivered substance to perform its intended task or the amount of drug needed to provide a therapeutic result. Therefore, an "effective amount" or "therapeutically effective amount" may be dependent on such biological factors. The determination of an effective amount or therapeutically effective amount is well-within the ordinary skill in the art of pharmaceutical and medical sciences based on known techniques in the art as well as the present disclosure. See for example, Curtis L. Meinert & Susan Tonascia, *Clinical Trials: Design, Conduct, and Analysis,* Monographs in Epidemiology and Biostatistics, vol. 8 (1986).

As used herein, "drug," "active agent," "bioactive agent," "pharmaceutically active agent," "therapeutically active agent" and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category, it is understood that such recitation is intended to include the active agent per se, as well as pharmaceutically acceptable salts, or compounds significantly related thereto, including without limitation, prodrugs, active metabolites, isomers, and the like.

As used herein, "cellular energy inhibitor" refers to a compound that inhibits glycolysis and mitochondria function of a cancer cell.

As used herein, "glycolysis inhibitor" refers to a compound that inhibits, reduces, or stops, glycolysis in a cancer cell.

As used herein, "mitochondria inhibitor" refers to a compound that inhibits, reduces, or stops mitochondria function in a cancer cell.

As used herein, "hexokinase 1" or "hexokinase 1 isozyme" refers to any isoforms of hexokinase 1 and its naturally known variants, including those provided in SEQ ID NO: 1, SEQ ID NO: 2, SEQ ID NO: 3, and SEQ ID NO: 4.

As used herein, "hexokinase 2" or "hexokinase 2 isozyme" refers to any isoforms of hexokinase 2 and its naturally known variants, including that provided in SEQ ID NO: 5.

As used herein, the terms "dosage form", "formulation" and "composition" are used interchangeably and refer to a mixture of two or more compounds, elements, or molecules. In some aspects the terms "dosage form", "formulation" and "composition" may be used to refer to a mixture of one or more active agents with a carrier or other excipients.

As used herein, "carrier" or "pharmaceutically acceptable carrier" refers to a substance with which a drug may be combined to achieve a specific dosage formulation for delivery to a subject. In the some aspects of the present invention, the carriers used may or may not enhance drug delivery. As a general principle, carriers do not react with the drug in a manner which substantially degrades or otherwise adversely affects the drug, except that carriers may react with a drug to prevent it from exerting a therapeutic effect until the drug is released from the carrier. Further, the carrier, or at least a portion thereof must be suitable for administration into a subject along with the drug.

As used herein, the terms "release", "release rate" 'dissolution" "dissolution rate", are used interchangeably to refer to the discharge or liberation of a substance, including without limitation a drug, from the dosage form into a surrounding environment such as an aqueous medium either in vitro or in vivo.

As used herein, "controlled release," "sustained release," "modified release," "delayed release", "extended release" and "non-immediate release" are used interchangeably and refer to release of active agent or agents from a dosage form into the target environment or medium over a period of time that is at least 5% slower than the equivalent dosage containing immediate release (IR) formulations. In one embodiment, the "controlled release," "sustained release," "modified release" delayed release" "extended release" or non-immediate release" systems or compositions can provide for a release of the active agent or agents from the dosage form into the target environment or medium over a period of time that is at least 10 wt % slower than the equivalent dosage form containing immediate release (IR) formulations.

As used herein, "release modifying agent", "release modulating agent", and "release modifiers" are used interchangeably and refer to pharmaceutically acceptable agents or devices that are capable to alter, increase or decrease, or otherwise customize, the release rates of at least one of the contents of the compositions or dosage forms thereof, when exposed to an aqueous use environment.

As used herein, "admixed" means that at least two components of the composition can be partially or fully mixed, dispersed, suspended, dissolved, or emulsified in one another. In some cases, at least a portion of the drug may be admixed in at least one carrier substance.

As used herein, "adverse drug experience" refers to any adverse event associated with the use of a drug in a subject, including the following: an adverse event occurring in the course of the use of a drug product in professional practice; an adverse event occurring from drug overdose whether accidental or intentional; an adverse event occurring from drug abuse; an adverse event occurring from drug withdrawal; and any failure of expected pharmacological action. The adverse drug experience may lead to a substantial disruption of a person's ability to conduct normal life functions. In some instances, the adverse drug experience may be serious or life threatening.

While some of the adverse drug experiences may be expected, in some instances, such experiences may be unexpected. "Unexpected," refers to an adverse drug experience that has not been previously catalogued by a responsible governmental agency (such as the Food and Drug Administration of the United States) and or not provided in the current labeling for the drug product.

The unexpected adverse experiences may include events that may be symptomatically and pathophysiologically related to a known event, but differ from the event because of greater severity or specificity. For example, under this definition, hepatic necrosis would be unexpected (by virtue of greater severity) if the known event is elevated hepatic enzymes or hepatitis. Similarly, cerebral thromboembolism and cerebral vasculitis would be unexpected (by virtue of greater specificity) if the known event is cerebral vascular accidents. For a more comprehensive definition and description of adverse drug experience, see 21 C.F.R. §314.80, which is incorporated by reference in its entirety.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still contain such an item as long as there is no measurable effect thereof Unless otherwise, indicated "substantially" preventing hydrolysis or hydrolyzing refers to the ability of sugar(s) to stabilize the cellular energy inhibitor for at least one hour while such that at least 50% of the cellular energy inhibitor does not hydrolyze.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3.5, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

For example, a concentration range of 0.5 to 15 mM should be interpreted to include not only the explicitly recited concentration limits of 0.5 mM and 15 mM, but also to include individual concentrations within that range, such as 0.5 mM, 0.7 mM, 1.0 mM, 5.2 mM, 11.6 mM, 14.2 mM, and sub-ranges such as 0.5-2.5 mM, 4.8-7.2 mM, 6-14.9 mM, etc. This interpretation should apply regardless of the breadth of the range or the characteristic being described.

It has been recognized by the present inventor that an alternative to tradition anti-cancer compositions and treatments can be achieved by targeting the energy production of a cancer cell. Without intending to be bound by any particular theory, the present inventor has found that certain cellular energy inhibitors can be used to treat cancers. Generally, there are two energy (ATP) production factories inside the cell, i.e., glycolysis and oxidative phosphorylation by mitochondria. In normal cells, about 5% of the total cellular energy (ATP) production is derived from glycolysis and about 95% from the mitochondria. In cancer cells, the energy production by glycolysis can be significantly increased (up to 60%). This dramatic increase in glycolysis in cancer cells results in a significant increase in lactic acid production.

Most cancers (>90%) exhibit this common metabolic phenotype. This is called the "Warburg Effect", i.e., significant increase in glycolysis in cancer cells even in the presence of oxygen. The most frequent cancer detection method used clinically, i.e., Positron Emission Tomography (PET) is based on this metabolic phenotype, i.e., the "Warburg effect". Cancer cells that exhibit the "Warburg effect" pump out the produced lactic acid via a transporter (i.e., monocarboxylate transport isoforms). The number of these transporters (considered as doors or gates) in cancer cells is much greater than in normal cells.

Figure 2:
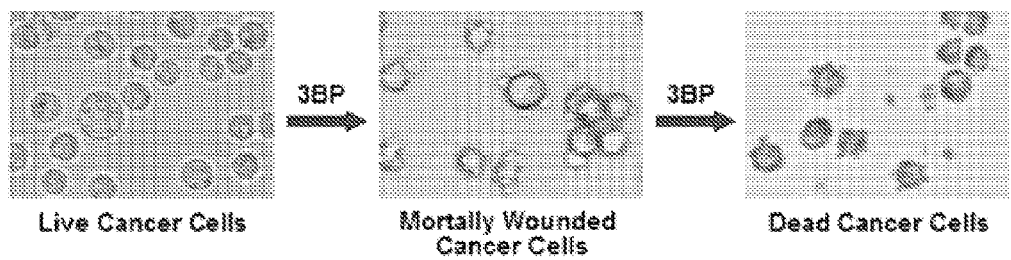
FIG. 2 is a series of photographs of cancer cells treated with 3-bromopyruvate in accordance with an embodiment of the present invention.

The presently disclosed cellular energy inhibitors, shown as 3-bromopyruvate (3BP) (a lactic acid analog) in FIG. 1, are small chemicals and can mimic the lactic acid chemical structure; depicted as a small diamond in FIG. 1. Therefore, cellular energy inhibitors disguised as lactic acid can "trick" the cancer cells and enter like a Trojan horse (FIG. 1). The inhibitors have little effect on normal cells as these contain very few lactic acid transporters. Because of the present cellular energy inhibitors' highly reactive nature, it can destroy the two energy production factories (FIG. 1; one diamond above the hexokinase (HK), shown as 3BP is destroying one energy production factory, i.e., glycolysis, and another red diamond inside the mitochondrion means that 3BP is destroying also this energy production factory). As a result, the cellular energy (ATP) can be depleted very rapidly by cellular energy inhibitors; 3BP in FIG. 1, attack the two factories at the same time causing the cancer cells to rapidly explode (cell membrane rupturing). An example of this can be seen in FIG. 2, which shows liver cancer cells treated with 3BP. Here, the healthy cancer cells are round and iridescent (left picture). However, when they are treated with 3BP, the cell membranes rupture (middle picture) and then die (see cell debris in the far right picture).

Figure 3:
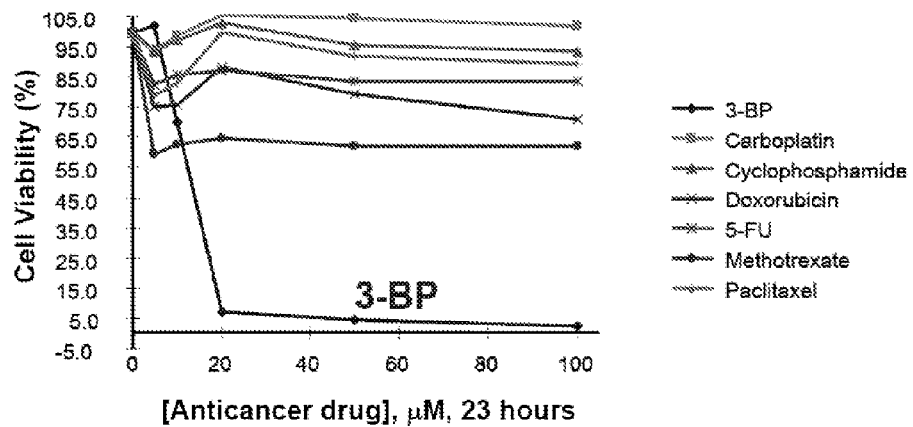
FIG. 3 is a plot of cell viability for hepatocellular carcinoma vs. µM of various anti-cancer agents in accordance with an embodiment of the present invention.

FIG. 3 depicts a cancer killing mechanism by 3BP in accordance with an embodiment of the present invention. Unlike most normal cells, cancer cells produce elevated amounts of lactic acid (Warburg Effect). Therefore, lactic acid transporters (mono carboxylate transporters) are up-regulated in cancer cells. Because 3BP is structurally similar to that of lactic acid, it is able to enter preferentially cancer cells (normal cells are spared). Once inside the cancer cells, 3BP inhibits the two power plants (glycolysis and mitochondria), depicted as X. The cellular energy (ATP) reserves of the cancer cells are then rapidly depleted. This leads to cell membrane rupture, blebbing, and cell death (Apoptosis/Necrosis) resulting in tumor shrinkage and disappearance.

In accordance with this, the present disclosure allows for safe administration and use of the present anti-cancer compositions that comprise a cellular energy inhibitor having the structure according to formula I

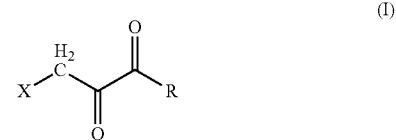

(I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C$_{12}$ heteroaryl, H, and an alkali metal; where R' represents H, alkali metal, C1-C6 alkyl, C6-C12 aryl or C(O)R''', R'' represents H, C1-C6 alkyl, or C6-C12 aryl, and R''' represents H, C1-C20 alkyl or C6-C12 aryl. Additionally, the anti-cancer composition can comprise at least one sugar, which stabilizes the cellular energy inhibitor by substantially preventing the inhibitor from hydrolyzing. The anti-cancer composition can further comprise a hexokinase inhibitor. Further, the anti-cancer composition can also comprise a biological buffer that is present in an amount sufficient to at least partially deacidify the cellular energy inhibitor and neutralize metabolic by-products of the cellular energy inhibitor. The anti-cancer composition can further comprise a glycolysis inhibitor.

The present inventor has recognized the need to provide safe and efficacious compositions that allow for treatment of cancers. As previously discussed, the present cellular energy inhibitors can be stabilized by the use of at least one sugar such that the sugar substantially prevents hydrolysis of the cellular energy inhibitor. In this way, the sugar can stabilize the cellular energy inhibitor for at least 1 hour such that at least 50% of the inhibitor does not hydrolyze. In another embodiment, the at least one sugar can stabilize the cellular energy inhibitor for at least 1 hour and prevent at least 95% of the inhibitor from hydrolyzing. In yet another embodiment, the at least one sugar can stabilize the cellular energy inhibitor for at least 2 hours such that at least 95% of the inhibitor does not hydrolyze.

The anti-cancer compositions disclosed herein generally include a compound as described by formula (I). In one embodiment, R of formula (I) can be OH and X of formula (I) can be selected from the group consisting of: a nitro, an imidazole, a halide, a sulfonate, a carboxylate, an alkoxide, and an amine oxide. Additionally, X can be a halide selected from the group consisting of: fluoride, bromide, chloride, and iodide. In one embodiment, X can be a sulfonate selected from the group consisting of: triflate, mesylate and tosylate. In another embodiment, X can be amine oxide. In still another embodiment, the amine oxide can be dimethylamine oxide.

In one embodiment, the cellular energy inhibitor can be a 3-halopyruvate and can be selected from the group consisting of: 3-fluoropyruvate, 3-chloropyruvate, 3-bromopyruvate, 3-iodopyruvate, and combinations thereof. The anti-cancer composition can comprise the cellular energy inhibitor in a concentration from about 0.1 mM to about 25.0 mM. In one embodiment, the anti-cancer composition can comprise the cellular energy inhibitor in a concentration from about 1.0 mM to about 10.0 mM.

Figure 6:
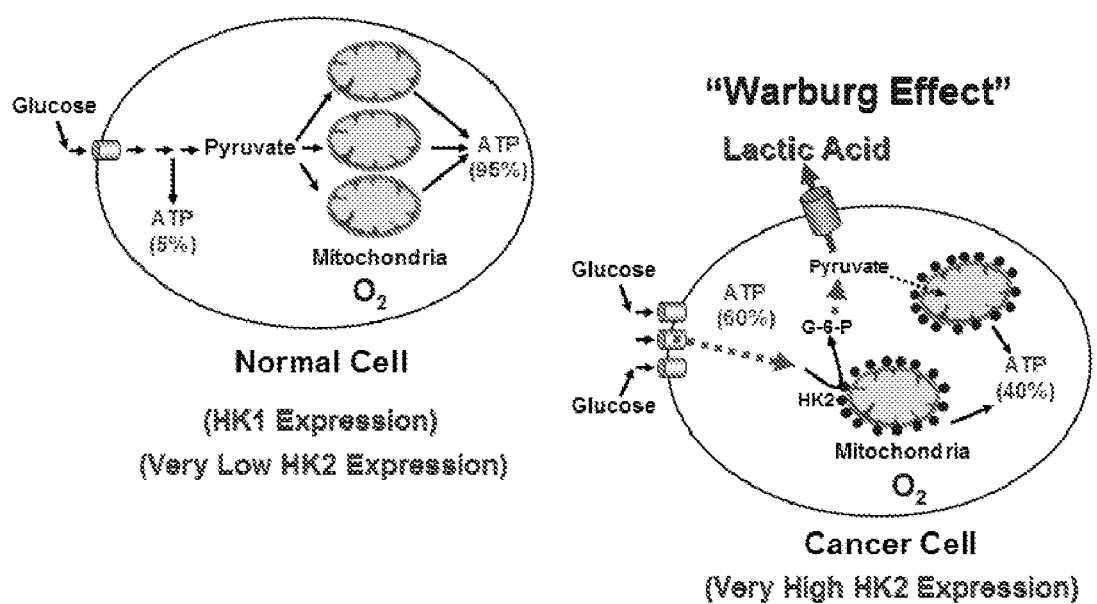
FIG. 6 is a schematic for normal and cancer cell energy production in accordance with an embodiment of the present invention.
Figure 7:
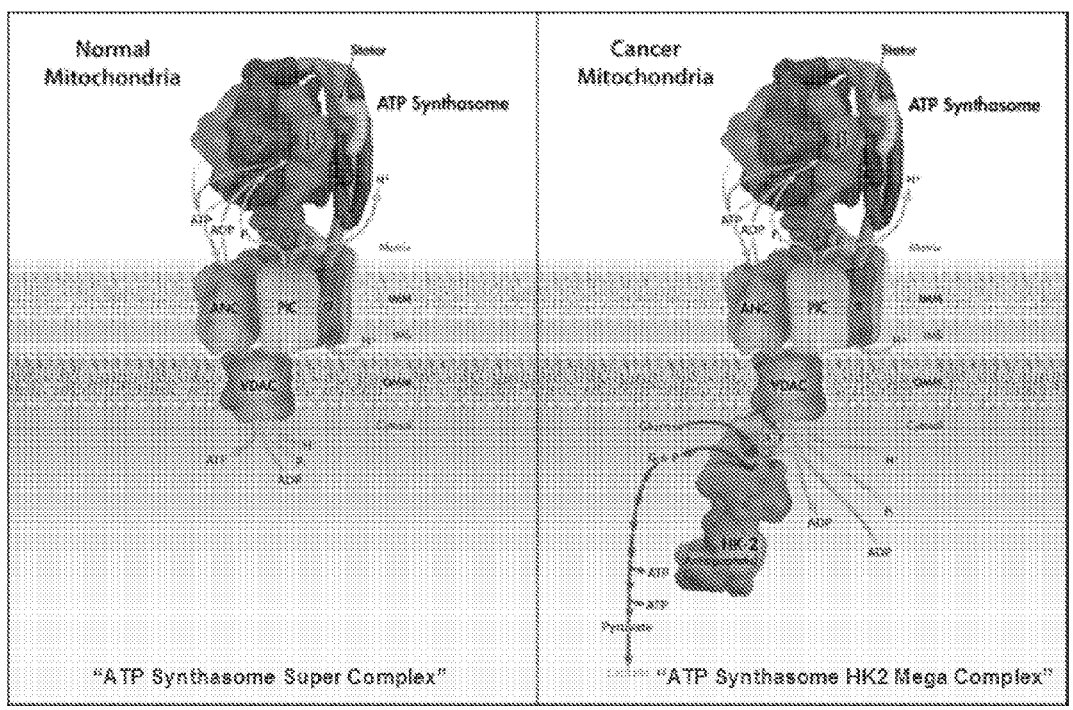
FIG. 7 is a schematic of normal and cancer mitochondria with an embodiment of the present invention.
Figure 8:
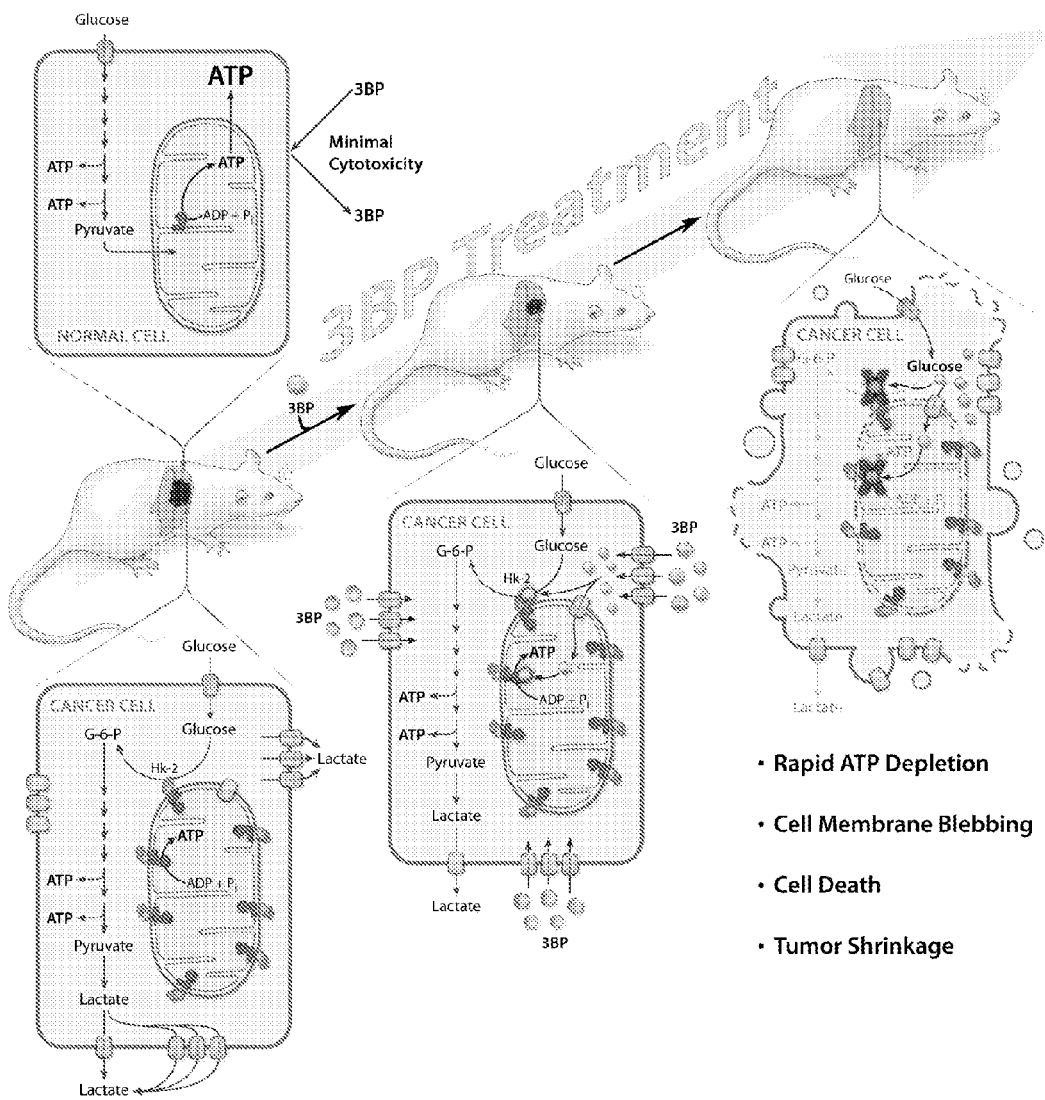
FIG. 8 is a schematic of a cancer killing mechanism in accordance with an embodiment of the present invention.

The hexokinase inhibitor can be any inhibitor that inhibits hexokinase 1 (HK1) and/or hexokinase 2 (HK 2). In one embodiment, the hexokinase inhibitor can be up to 25 amino acid units from the N-terminal region of Hexokinase 2 isozyme or Hexokinase 1 isozyme. In one embodiment, the hexokinase inhibitor can be an amino acid sequence of 5 to 20 amino acid units, said 5 to 20 amino acid sequence being present in the first 25 amino acid unit region beginning from the N-terminal end of hexokinase 1 isozyme or hexokinase 2 isozyme. Such amino acid sequences can displace cellular bound hexokinase, or competitively bind to voltage dependent anion channels (VDAC) and thus prevent initial hexokinase binding (as shown in FIGS. 6 and 7). FIGS. 6 and 7 depict the metabolic difference between normal and cancer cells. The major source of ATP production is from the mitochondria in normal cells. However, ATP production from glycolysis becomes important in cancer cells. The cancer cell mitochondria depict many bound HK2 or HK1 molecules. These in complex with VDAC and the ATP synthasome are called the "ATP synthasome mega complex", while normal cell mitochondria exist with little or no HK2 or HK1 bound. The latter complex is called the "ATP synthasome super complex". As such, the use of the present hexokinase inhibitors can prevent the formation of the ATP synthasome mega complex. The hexokinase inhibitor can also include humanized antibodies against the N-terminal region of HK1 or HK 2. In one embodiment, the hexokinase inhibitor can be an amino acid sequence, such as SEQ ID NO: 6, corresponding to the first 25 amino acids from the N-terminus end of hexokinase 1 (isoform 1) having a sequence as found in FIG. 10. In another embodiment, the hexokinase inhibitor can be an amino acid sequence, SEQ ID NO: 7, corresponding to the first 25 amino acids from the N-terminus end of hexokinase 1 (isoform 2) having a sequence of as found in FIG. 11. In still another embodiment, the hexokinase inhibitor can be an amino acid sequence, SEQ ID NO: 8, corresponding to the first 25 amino acids from the N-terminus end of hexokinase 1 (isoform 3) having a sequence of as found in FIG. 12. In yet another embodiment, the hexokinase inhibitor can be an amino acid sequence, SEQ ID NO: 9, corresponding to the first 25 amino acids from the N-terminus end of hexokinase 1 (isoform 4) having a sequence of as found in FIG. 13. In yet another embodiment, the hexokinase inhibitor can be an amino acid sequence, SEQ ID NO: 10, corresponding to the first 25 amino acids from the N-terminus end of hexokinase 2 having a sequence of as found in FIG. 14. Additional hexokinase inhibitors can be those as disclosed in U.S. Pat. No. 5,854,067 (to Newgard et al, issued Dec. 29, 1998) and/or U.S. Pat. No. 5,891,717 (to Newgard et al., issued Apr. 6, 1999), both of which are incorporated by reference in their entireties. Additional hexokinase inhibitors that can be used in the present invention include those disclosed in U.S. Pat. Nos. 6,670,330; 6,218,435; 5,824,665; 5,652,273; and 5,643,883; and U.S. patent application publication Nos. 20030072814; 20020077300; and 20020035071; each of the foregoing patent publications and patent application is incorporated herein by reference, in their entireties.

While the anti-cancer composition generally comprises at least one sugar, in one embodiment, the anti-cancer composition can comprise other sugars, such as a second sugar. In another embodiment, the anti-cancer composition can comprise a third sugar. The sugars described herein can include their analogues. In one embodiment, the sugar can be gluconic acid. In another embodiment, the sugar can be glucuronic acid. At least one of the sugars can be a five-carbon sugar. In one embodiment, at least two of the sugars can be five-carbon sugars. The five-carbon sugars can be independently selected from the group consisting of mannitol, erytritol, isomalt, lactitol, maltitol, sorbitol, xyolitol, dulcitol, ribitol, inositol, sorbitol, and combinations thereof. In one embodiment, at least one of the sugars can be glycerol. In another embodiment, the sugars can be glycerol, inositol, and sorbitol. The anti-cancer composition can comprise glycerol in a range from about 0.1 wt % to about 3 wt %, inositol in a range from about 1 wt % to about 5 wt %, and sorbitol in a range from about 30 wt % to about 50 wt %. Additionally, each of the sugars may be added in a volume up to a maximum solubility of the sugar in the formulation or composition.

The sugars described herein can be any isomeric form. In one embodiment, the anti-cancer compositions described herein can include the less biologically active form of the sugar as compared to its isomer. In one aspect, the less biologically active sugar can be the L-enantiomer sugar. However, if the D-enantiomer sugar is found to be less biologically active as compared to its L form, then the D form can be used. In one embodiment, such sugars can function as a glycolytic inhibitor.

In one embodiment, the anti-cancer composition can comprise the at least one sugar in a concentration from about 0.1 mM to about 250 mM. In another embodiment, the anti-cancer composition can comprise the at least one sugar in a concentration from about 0.5 mM to about 25 mM.

Generally, the anti-cancer composition can comprise a glycolysis inhibitor. In one embodiment, the glycolysis inhibitor can be 2-deoxglucose. The anti-cancer composition can comprise the glycolysis inhibitor in a concentration from about 0.1 mM to about 25.0 mM. In one embodiment, the anti-cancer composition can comprise the glycolysis inhibitor in a concentration from about 1 mM to about 5 mM.

Generally, the anti-cancer composition can include a biological buffer that is present in an amount sufficient to at least partially deacidify the cellular energy inhibitor and neutralize metabolic by-products of the cellular energy inhibitor. In one embodiment, the biological buffer can be selected from the group consisting of a citrate buffer, a phosphate buffer, and an acetate buffer. In another embodiment, the biological buffer can be a citrate buffer. In still another embodiment, the biological buffer can be sodium citrate.

As discussed herein, the cellular energy inhibitor is delivered to a cancer cell and is taken up by the cell. After metabolism of the cellular energy inhibitor, the cellular energy inhibitor can cause by-products. In one embodiment, the by-product can be a hydrogen halide. Additionally, the hydrogen halide can be hydrogen bromide or hydrogen iodide. In one embodiment, the hydrogen halide can be hydrogen bromide.

The anti-cancer composition can comprise the biological buffer in a concentration of from about 0.1 mM to about 200 mM. In one embodiment, the anti-cancer composition can comprise the biological buffer in a concentration of from about 1 mM to about 20 mM. Additionally, the biological buffer can maintain a physiological pH of 4.0 to 8.5. In one embodiment, the biological buffer can maintain a physiological pH of 5.5 to 8.0. In another embodiment, the biological buffer can maintain a physiological pH of 6.8 to 7.8. In still another embodiment, the biological buffer can maintain a physiological pH of 7.3 to 7.6.

In addition to the above components, the anti-cancer compositions described herein can further comprise a halo monocarboxylate compound that is separate from the cellular energy inhibitor. In the cases where the halo monocarboxylate compound can function to inhibit glycolysis and mitochondria function, the halo monocarboxylate can be considered a second cellular energy inhibitor. In one embodiment, the halo monocarboxylate compound can be a halo two-carbon monocarboxylate compound. The halo two-carbon monocarboxylate compound can be selected from the group consisting of 2-fluoroacetate, 2-chloroacetate, 2-bromoacetate, 2-iodoacetate, and mixtures thereof. In one embodiment, the halo two-carbon monocarboxylate compound can be 2-bromoacetate. The anti-cancer composition can comprise the halo two-carbon monocarboxylate compound in a concentration from about 0.01 mM to about 5.0 mM. In one embodiment, the anti-cancer composition can comprise the halo two-carbon monocarboxylate compound in a concentration from about 0.1 mM to about 0.5 mM.

Additionally, the halo monocarboxylate compound can be a halo three-carbon monocarboxylate compound. In one embodiment, the halo three-carbon monocarboxylate compound can be selected from the group consisting of 3-fluorolactate, 3-chlorolactate, 3-bromolactate, 3-iodolactate, and mixtures thereof. The anti-cancer composition can comprise the halo three-carbon monocarboxylate compound in a concentration from about 0.5 mM to about 250 mM. In one embodiment, the anti-cancer composition can comprise the halo three-carbon monocarboxylate compound in a concentration from about 10 mM to about 50 mM.

The anti-cancer compositions described herein can further comprise an antifungal agent and/or antibacterial agent. In one embodiment, the anti-cancer composition can individually comprise the antifungal agent and/or antibacterial agent in a concentration from about 0.01 mM to about 5.0 mM. In another embodiment, the anti-cancer composition can individually comprise the antifungal agent and/or antibacterial agent in a concentration from about 0.05 mM to about 0.5 mM.

The anti-cancer compositions described herein can further comprise a mitochondrial inhibitor in addition to the cellular energy inhibitor. The mitochondrial inhibitor can be selected from the group consisting of: oligomycin, efrapeptin, aurovertin, and mixtures thereof. In one embodiment, the anti-cancer composition can comprise the mitochondrial inhibitor in a concentration from about 0.001 mM to about 5.0 mM. In another embodiment, the anti-cancer composition can comprise the mitochondrial inhibitor in a concentration from about 0.01 mM to about 0.5 mM.

In addition to the above concentrations, the anti-cancer compositions can have various ratios of the components described herein. In one embodiment, the cellular energy inhibitor and biological buffer can be present in a ratio ranging from 1:1 to 1:5 by mM. In another embodiment, the cellular energy inhibitor and glycolysis inhibitor can be present in a ratio ranging from 5:1 to 1:1 by mM. In still another embodiment, the cellular energy inhibitor and the at least one sugar are present in a ratio ranging from 1:1 to 1:5 by mM. In yet another embodiment, the cellular energy inhibitor and the halo two-carbon monocarboxylate compound can be present in a ratio ranging from 20:1 to 4:1 by mM. In still yet another embodiment, the cellular energy inhibitor to mitochondrial inhibitor can be present in a ratio ranging from 20:1 to 40:1 by mM.

As described above, the present anti-cancer compositions can comprise antifungal agents, antibiotics, glycolysis inhibitors, inhibitors of mitochondria, sugars, and biological buffers. Examples of such agents include, but are not limited to, amphotericin B, Efrapeptin, doxorubicin, 2-deoxyglucose (2DOG), d-lactic acid, analogs of 2DOG, dicholoracetic acid (or salt form of dichloroacetate), oligomycin, analogs of oligomycin, glycerol, inositol, sorbitol, glycol, erythritol, threitol, arabitol, xylitol, ribitol, mannitol, dulcitol, iditol, isomalt, maltitol, lactitol, polyglycitol, sodium phosphate, sodium citrate, sodium acetate, sodium carbonate, sodium bicarbonate, sodium pyruvate, sodium lactate, oxaloacetate, isocitrate, aconitate, succinate, fumarate, malate, diluted saline solutions with varying concentrations of NaCl, and water. In addition to the sodium ion that accompanies these biological buffers, calcium and potassium cations can also accompany the biological buffers. The active agents of the anti-cancer composition can include the cellular energy inhibitor, the glycolysis inhibitor, the mitochondria inhibitor, the halo monocarboxylate compound, the antifungal agent, and the antibiotic agent.

The anti-cancer composition can further include various additives. In one embodiment, the anti-cancer compositions can include immune system modulators and/or immune system boosters. Such immune system modulators and/or immune system boosters can include d-lactic acid, epinephrine, brown rice extract, muramyl dipeptide including analogues, mushroom extract, bioflavonoids, Vitamin D3-Binding Protein-Derived Macrophage Activating Factor (GcMAF), inhibitors of nagalase, threonine attached to N-acetylgalactosamine, antibodies against nagalase, etc. Without being bound by any particular theory, flavonoids may have indirect anti-cancer effects. Specifically, increase in antioxidant capacity of blood seen after the consumption of flavonoid-rich foods is not caused directly by flavonoids themselves, but most likely is due to increased uric acid levels that result from metabolism of flavonoids. The body sees them as foreign compounds and is trying to get rid of them. This process of removing unwanted compounds includes Phase II enzymes that also help eliminate mutagens and carcinogens, and therefore may be of value in cancer prevention. Therefore, flavonoids could also induce mechanisms that help kill cancer cells and inhibit tumor invasion. In one embodiment, the present compositions can include d-lactic acid. In another embodiment, the present compositions can include epinephrine.

In one embodiment, the additives to the anti-cancer compositions can include phospholipids including liposomes and nanoparticles. The liposomes or nano-particles can incorporate annexin-A5 molecules or antibodies against phosphatidylserine. In this way, the rate of 3BP release can be controlled and its delivery can be targeted to cancer cells upon its administration. Liposomes can have a natural ability to target cancer. Without intending to be bound by any particular theory, the endothelial wall of all healthy human blood vessels is encapsulated by endothelial cells that are bound together by tight junctions. These tight junctions can stop any large particle(s) in the blood from leaking out of the vessel. Generally, tumor vessels do not contain the same level of seal between cells and are diagnostically leaky. In one embodiment, liposomes of certain sizes, typically less than 400 nm, can rapidly enter tumor sites from the blood, but are kept in the bloodstream by the endothelial wall in healthy tissue vasculature. Additionally, the additives to the anti-cancer compositions can include L-Lactate dehydrogenase or D-Lactate Dehydrogenase (or both forms of the enzymes) as well as nicotinamide adenine dinucleotides ($NAD^+$), which can be included in the present formulations to decrease the blood lactate concentration as well as the lactate concentration near tumor sites. By decreasing the blood lactate concentration in cancer patients, the highly glycolytic innate immune system can work appropriately.

In one embodiment, the additives to the anti-cancer compositions can include less biologically active amino acids as compared to their isomers to facilitate cancer cell starvation. In one aspect, the less biologically active amino acid can be a D-amino acid. However, if the L-amino acid is less biologically active than the D-form, the L-amino acid can be used.

In one embodiment, the additives to the anti-cancer compositions can include inhibitors for DNA replication; inhibitors for DNA binding; and inhibitors for DNA transcription. In another embodiment, the additives to the anti-cancer compositions can include inhibitors for cell cycle, growth and/or proliferation. In yet another embodiment, the additives to the anti-cancer compositions can include inhibitors for signal transduction pathways. In yet another embodiment, the additives to the anti-cancer compositions can include inhibitors for angiogensis. In yet another embodiment, the additives to the anti-cancer compositions can include small RNAs that interfere with normal gene control including antisense RNA, micro RNA, small hairpin RNA, short hairpin RNA, small interfering RNA. In yet another embodiment, the additives to the anti-cancer compositions can include vitamin C; nutritional supplements including vitamins, CoQ10, flavonoids, free fatty acid, alpha lipoic acid, acai, gogi, mango, pomergrante, L-carnitine, selenium; etc.

In addition to the active agent(s), the composition can also include a pharmaceutically acceptable carrier. The carrier can be a single composition, or a mixture of compositions. Additionally, the carrier can take the form of an encapsulation coat, an absorbing agent, a coating substance, a controlled release device, a release modifying agent, surfactants, or a combination thereof. In some aspects, the carrier can comprise about 1 wt % to about 99 wt % of the total composition. In one embodiment, the carrier can comprise about 5 wt % to about 95 wt % of the total formulation. In another embodiment, the carrier can comprise about 20 wt % to about 80 wt %. In yet a further embodiment, the carrier can comprise about 30 wt % to about 60 wt %. In one embodiment, the carrier can be admixed with the active agent(s). In another embodiment, the carrier can adsorb, entrap, or encapsulate at least a portion of the active agent(s).

Non-limiting examples of compounds that can be used as at least a part of the carrier include without limitation: cetyl alcohol and its esters; stearic acid and its glycerol esters, polyoxyethylene alkyl ethers; polyethylene glycol; polyglycolyzed glycerides; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; proteins; polyoxyethylene glycerides; polyoxyethylene sterols, derivatives, and analogues thereof; polyoxyethylene hydrogenated vegetable oils; reaction mixtures of polyols with at least one member of the group consisting of fatty acids, glycerides, vegetable oils, hydrogenated vegetable oils, and sterols; tocopherol derivatives, sugar esters; sugar ethers; sucroglycerides; waxes, shellac, pharmaceutically acceptable salts thereof, and mixtures thereof.

Non-limiting examples of release modifying agents include without limitation: polyethylene glycols having a weight average molecular weight of about 1000 and more, carbomer, methyl methacrylate copolymers, methacrylate copolymers, hydroxypropyl methyl cellulose, hydroxypropyl cellulose, cellulose acetate phthalate, ethyl cellulose, methyl cellulose and their derivatives; ion-exchange resin; mono-, di-, tri-esters of fatty acids with glycerol; tocopherol and its esters; sucrose esters with fatty acids; polyvinyl pyrollidone; xanthan gums; cetyl alcohol; waxes; fats and oils, proteins, alginate, polyvinyl polymers, gelatins, organic acids, and their derivatives and combinations thereof.

In one embodiment, the carrier can include at least one of celluloses; carbomers; methacrylates; dextrins; gums; inorganic carbonates or salts of calcium or magnesium or both; fatty acid esters; gelatin; lactoses; maltoses; mono-, di- or triglycerides; oils; polyethylene glycols; polyethylene oxide co-polymers; proteins; resins; shellac; silicates; starches; sugar stearates; partially or fully hydrogenated vegetable oils; waxes; and combinations thereof.

In yet another embodiment, the carrier can include at least one of celluloses; carbomers; methacrylates; inorganic carbonates or salts of calcium; inorganic carbonates or salts of magnesium; fatty acids; fatty acid esters; gelatin; lactoses; polyethylene glycol; polyethylene oxide co-polymers; silicates; partially or fully hydrogenated vegetable oils, and combinations thereof.

In yet a further embodiment, the carrier can include at least one of microcrystalline cellulose; hydroxypropyl methylcellulose; ethyl cellulose; silicon dioxide; magnesium aluminosilicate; lactose; xanthan gum; stearic acid; glyceryl distearate; hydrogenated vegetable oil; and combinations thereof.

The formulation, including any dosage form, can include other components or additives. Such additional components and additives are optional. In one aspect, the additive can be a solid at room temperature and have a melting point or range that is greater than about 40° C. Non-limiting examples of additives that can be included in the systems of the present invention include without limitation: fillers such as lactoses, starches, sugars, celluloses, calcium salts, silicon oxides, metallosilicates and the like; disintegrants such as starch glycolate, lauryl sulfate, pregaltinized starch, croscarmellose, crospovidone and the like; binders such as pyrrolidones, methacrylates, vinyl acetates, gums, acacia; tragacanth; kaolins; carrageenan alginates, gelatins and the like; cosolvents such as alcohols, polyethylene glycols having average molecular weight of less than 1000, propylene glycols and the like; surface tension modifiers such as hydrophilic or amphiphlic surfactants; taste-masking agents; sweeteners; microencapsulating agents; process aids such as lubricants, glidants, talc, stearates, lecithin and the like; polymeric coating agents; plasticizers; buffers; organic acids; antioxidants; flavors; colors; alkalizers; humectants; sorbitols; mannitols; osmotic salts; proteins; resins; moisture repelling agents; hygroscopic agents; desiccants; and combinations thereof.

The formulations of the present invention can be formulated into a variety of oral dosage forms including, but not limited to two piece hard gelatin capsules, soft gelatin capsules, beads, beadlets, granules, spherules, pellets, microcapsules, microspheres, nanospheres, nanocapsules, tablets, or combinations thereof. Other forms known to those of ordinary skill in the art may also be used. In one aspect, the oral dosage form may be a capsule or tablet. In another embodiment the oral dosage form may include a multi-component dosage form such as beads in a capsule, a capsule or capsules within a capsule, a tablet or tablets in a capsule, or a multi-layer tablet. It is noteworthy that, when the formulation includes multiple dosage forms, such dosage forms need not be the same. Further, such dosage forms may not be physically present together.

The dosage form, e.g. tablet, may be coated or enrobed with a hydrophilic or a hydrophobic coat material known in the art. In one embodiment, the coat can be a film coat, sugar coat, enteric coat, semipermeable coat, sustained release coat, delayed release coat, osmotic coat and the like. In a further embodiment, the coating material can be a cellulose, gelatin, methacrylate, polyvinyl acetate, povidone, polyethylene glycol, polyetyhylne oxide, poloxamers, carbomers, shellac, phthalate and the like and their derivatives and combinations thereof. In another embodiment, the coat is a dry powder coat. In one embodiment, the tablet can be a matrix tablet. It is noteworthy that, when present, the coat can be considered as part, or all, of the carrier component of the formulation.

In addition to the compositions described herein, a method for the treatment of cancer can comprise administering to a subject the anti-cancer compositions as described herein in a therapeutically effective amount. The anti-cancer composition can be administered to the subject when the subject's blood insulin/glucagon ratio is in the range of about 1 to about 10. Additionally, the anti-cancer composition can be administered to the subject after fasting for at least 4 hours. In one embodiment, the anti-cancer composition can be administered to the subject after fasting for 6 hours, and in another embodiment, after fasting for 8 hours. Additionally, the anti-cancer composition can be administered to the subject after fasting for 2 hours. It is noted that such times are not intended to be limiting, and that in one embodiment, the amount of time fasting can be such that the subject's blood insulin/glucagon ratio is in the range of about 2 to about 5.

In addition, the method of administration can be selected from the group consisting of: inter-arterially, intravenously, inter-peritoneally, inhalation, intra-tumorally, orally, topically, and subcutaneously. In one embodiment, the administration can be inter-arterially. The anti-cancer compositions can also be delivered by use of a feeding tube. Intra-tumorally delivery methods can include technologies involving a bronchoscope, an endoscope, and/or a colonoscopy, suppository to any openings, eye drops, nose drops, and ear drops. In one embodiment, the administration can be by intranasal delivery. Intranasal delivery can be used to bypass the blood brain barrier and can be particularly effective for tumors in the brain and/or spinal cord. In another embodiment, the administration can be by suppository. Suppository administration can be used for tumors in proximity to the rectal/anal area. Additionally, if intra-tumorally injection is going to be performed directly to/in the tumor, ultrasound imaging (or other imaging methods) can be used to aid this injection. In one embodiment, the administration can be by direct injection; e.g., to a prostate gland. Additionally, administration can be by an enema containing the composition described herein into the rectum and/or lower intestines. Chronic irrigation to treat obstructive colon, intestinal, or other obstructive cancers, can also be used in conjunction with the compositions described herein. In one embodiment, administration can also be by catheter to treat bladder cancers via the urethra. Further, intravenous delivery can be combined with a hemodialysis apparatus (i.e. kidney dialysis equipment) to destroy the metastatic circulating cancer cells outside of the blood vessels. In addition, both intravenous and inter-peritoneal can be assisted by utilization of a port system. Furthermore, the present anti-cancer composition can be immediate release, controlled release, or time controlled release. For time controlled release, the present compositions can delivered by implanting wafers, diamond chips, and other implantable devices near or on the tumor site.

Generally, when the anti-cancer composition is administered intra-arterially or intravenously, the administration can be for a duration from about 30 minutes to about 8 hours. In one embodiment, the anti-cancer composition can be intra-arterially or intravenously administered for a duration from about 3 hours to about 5 hours. Additionally, the administration of the anti-cancer composition can be part of a dosing regimen. In one embodiment, the administration can include a regimen lasting from about 1 week to 24 weeks. In another embodiment, the regimen can last from about 4 weeks to 8 weeks.

Generally, the present anti-cancer composition is administered in a therapeutically effective amount as defined herein. In one embodiment, the therapeutically effective amount can include a dosage of, or equivalent to, about 1 mM to about 10 mM of the anti-cancer composition in a volume of 25 ml to 1000 ml.

Figure 5:
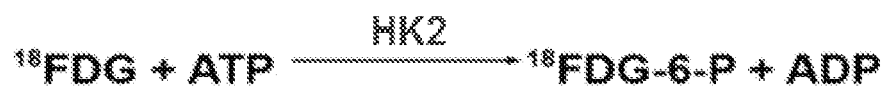
FIG. 5 is a reaction scheme for PET scanning in accordance with an embodiment with the present invention.
Figure 9:
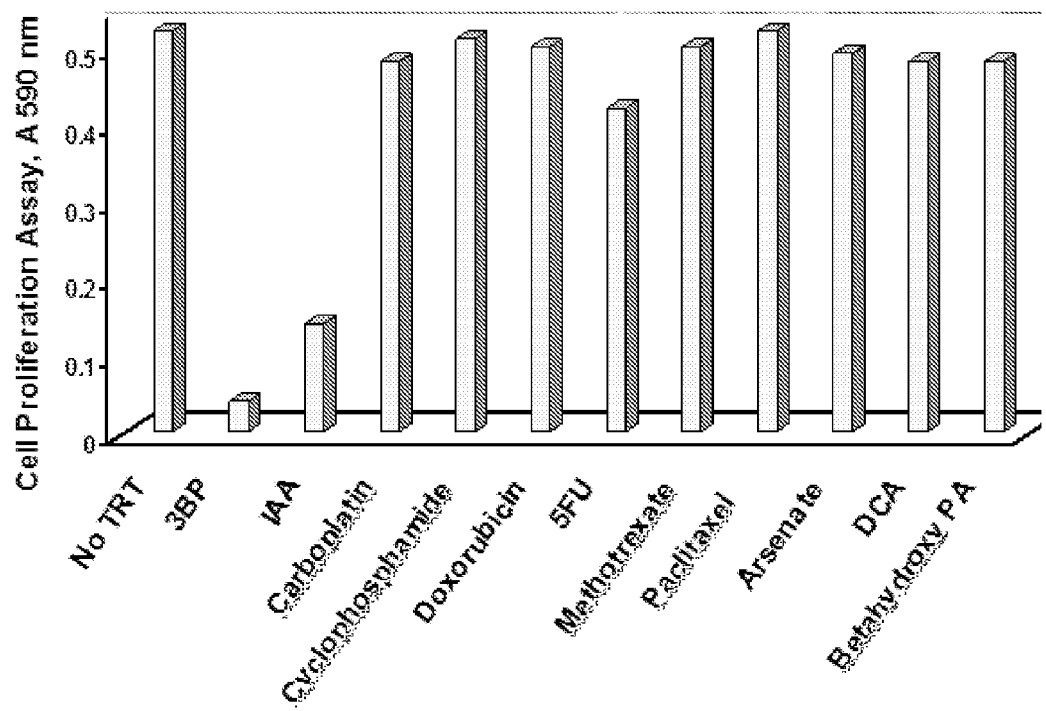
FIG. 9 is a bar graph of cell viability for human prostate cancer cells vs. various anti-cancer agents in accordance with an embodiment of the present invention.

The anti-cancer compositions described herein can be used to treat any cancer having increased glycolysis; the metabolic phenotype referred to as the "Warburg Effect", as described above. In another embodiment, the anti-cancer compositions can be used to treat any cancer that can be detected by Positron Emission Tomography (PET), which detects this metabolic phenotype. For example, FIG. 5 illustrates a reaction scheme for PET scanning. Human cancer cell lines that the present anti-cancer composition has shown to be effective against include liver, cervical, ovarian, lung, breast, colon, neuroblastoma, medulloblastoma, prostate, skin, pancreatic, childhood fibrolamellar hepatocellular carcinoma (FHCC), hepatocellular carcinoma (HCC), non small cell lung cancer. For example, FIG. 9 depicts a bar graph showing various cancer drugs effects on human prostate cancer cells. As seen in FIG. 9, 3-bromopyruvate is better than other known chemo-agents in stopping cancer cell proliferation. As such, the present cancers that can be treated with the present anti-cancer compositions can be selected from the group consisting of liver, cervical, ovarian, lung, breast, colon, neuroblastoma, medulloblastoma, prostate, skin, pancreatic, childhood fibrolamellar hepatocellular carcinoma (FHCC), hepatocellular carcinoma (HCC), non small cell lung cancer. The present anti-cancer compositions have been used to treat human cancer patients having childhood fibrolamellar hepatocellular carcinoma (FHCC), hepatocellular carcinoma (HCC), non small cell lung cancer, colon cancer, breast cancer, and pancreatic cancer. As such, cancers that can be treated with the present anti-cancer compositions can be selected from the group consisting of childhood fibrolamellar hepatocellular carcinoma (FHCC), hepatocellular carcinoma (HCC), non small cell lung cancer, colon cancer, breast cancer, pancreatic cancer, and combinations thereof.

In one embodiment, the anti-cancer composition can be used to treat liver cancer. In another embodiment, the anti-cancer composition can be used to treat cervical cancer. In still another embodiment, the anti-cancer composition can be used to treat ovarian cancer. In still another embodiment, the anti-cancer composition can be used to treat lung cancer. In still another embodiment, the anti-cancer composition can be used to treat breast cancer. In still another embodiment, the anti-cancer composition can be used to treat colon cancer. In still another embodiment, the anti-cancer composition can be used to treat neuroblastoma. In still another embodiment, the anti-cancer composition can be used to treat medulloblastoma. In still another embodiment, the anti-cancer composition can be used to treat prostate cancer. In still another embodiment, the anti-cancer composition can be used to treat skin cancer. In still another embodiment, the anti-cancer composition can be used to treat breast cancer. In still another embodiment, the anti-cancer composition can be used to treat pancreatic cancer. In still another embodiment, the anti-cancer composition can be used to treat childhood fibrolamellar hepatocellular carcinoma (FHCC). In still another embodiment, the anti-cancer composition can be used to treat hepatocellular carcinoma (HCC). In still another embodiment, the anti-cancer composition can be used to treat small cell and non small cell lung cancer. In still other embodiments the anti-cancer composition can be used to treat vaginal, anal, testicular, nasal, throat, mouth, esophageal, and brain cancers.

In addition to the above treatment of cancer, the present invention provides a method of minimizing toxicity of a cellular energy inhibitor of formula (I) to a subject receiving the cellular energy inhibitor comprising, combining in the subject, the cellular energy inhibitor with a biological buffer that is present in an amount sufficient to at least partially deacidify the cellular energy inhibitor and neutralize metabolic by-products of the cellular energy inhibitor due to its chemical reaction and/or cellular metabolism:

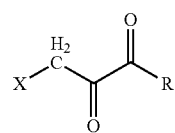

(I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R'' represents H, C1-C6 alkyl, or C6-C12 aryl, and R''' represents H, C1-C20 alkyl or C6-C12 aryl. In one embodiment, the cellular energy inhibitor and the biological buffer can be combined prior to administration to the subject.

Additionally, a method of minimizing an adverse drug experience associated with administration of an anti-cancer composition to a subject can comprise administering the anti-cancer composition to the subject at a time when the subject's blood insulin/glucagon ratio is in a range of about 1 to about 10, measured in picomolar (pM). The anti-cancer composition can be any anti-cancer composition described herein. In one embodiment, the insulin/glucagon ratio can be in a range of about 2 to about 5. Without intending to be bound by any particular theory, by administering the present anti-cancer compositions at a time where the subject's blood sugar is low, or the blood insulin/glucagon ratio is low, the normal cells can be protected against any incidental uptake of the anti-cancer active agents. Specifically, such administration can protect the hexokinase 2 (HK-2) enzyme that is present in normal tissues in small amounts. Under low blood sugar conditions, the HK-2 enzyme tends to enter the nucleus of normal cells rather than the cytosolic compartment. The nuclear location of HK-2 provides additional protection against chemo-agents such as 3-bromopyruvate, 2-bromoacetate, and 2-iodoacetate. As discussed herein, the administration can include a therapeutically effective amount of the anti-cancer composition. In one embodiment, the adverse drug experience can be cachexia. In another embodiment, the adverse drug experience can be pain.

Further, a method for assessing killing efficacy of an anti-cancer composition in a subject can comprise measuring a lactic acid level in the subject prior to administration of the anti-cancer composition; administering the anti-cancer composition to the subject; measuring the lactic acid level in the subject after administration of the anti-cancer composition; and determining the killing efficacy by measuring and/or correlating the difference between the lactic acid levels as a function of treatment time. The anti-cancer composition can be any of those described herein.

The lactic acid levels can be measured from a biological fluid from the subject. In one embodiment, the biological fluid can be selected from the group consisting of: blood and blood fractions, tears, sweat, urine, ascitic fluid, saliva, and combinations thereof. Additionally, the measuring can be colormetric using lactic acid binding enzymes. In one embodiment, the measuring can be by dip-stick or strip methods. In another embodiment, the measuring can be by magnetic resonance imaging.

In certain embodiments, the above-described anti-cancer compositions can comprise one or more of the cellular energy inhibitors, glycolysis inhibitors, mitochondria inhibitors, halo monocarboxylate compounds, and a second chemotherapeutic agent.

The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Further, the following additional drugs may also be used in combination with the antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons α, β, and γ; hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; Lhymosin-α-1; γ-globulin; superoxide dismutase (SOD); complement factors; anti-angiogenesis factors; antigenic materials; and pro-drugs.

Preferred chemotherapeutic agents for use with the compositions and methods of treatment described herein include, but are not limited to altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interferon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

All of the above drugs and additives may be added individually, in combination, as long as there is no negative interaction between or among the various drugs.

Additionally, the present invention provides kits for the treatment of cancer. The present kits provide the necessary ingredients with instructions such that one of ordinary skill in the art can combine the ingredients into an appropriate dosage form for delivery to a subject. At a minimum, a kit would include a cellular energy inhibitor ingredient, at least one sugar ingredient, a glycolysis inhibitor ingredient, a biological buffer ingredient, a container, and a set of instructions. Typically, the ingredients can be admixed such that the dosage form can be administered to a subject for the treatment of cancer. As described herein, such dosage can be part of a regimen for the treatment of various cancers.

In one embodiment, a kit for treatment of cancer can comprise a) a cellular energy inhibitor ingredient having the structure according to formula I

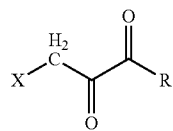
(I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl; b) at least one sugar ingredient, which stabilizes the cellular energy inhibitor ingredient by substantially preventing the cellular energy inhibitor ingredient from hydrolyzing; c) a glycolysis inhibitor ingredient; d) a biological buffer ingredient that is present in an amount sufficient to at least partially deacidify the cellular energy inhibitor ingredient and neutralize metabolic by-products of the cellular energy inhibitor ingredient; e) a container for containing the ingredients; and f) a set of instructions for the preparation of a dosage form using the ingredients and for administration of the dosage form to a subject.

In one embodiment, the ingredients can be further contained in individual containers inside the container.

In one embodiment, the kit can further contain a syringe filter for sterilization of at least one ingredient and sterile gloves.

In one embodiment, the kit can contain the cellular energy inhibitor in powdered form in an amount that provides a concentration of about 2.5 mM to about 5.0 mM when added to the solution.

In addition to the above, the ingredients of the kit can be modified as described herein.

Further, the present invention provides a use of a cellular energy inhibitor in the manufacture of an anti-cancer medicament for the treatment of a cancer, wherein the anti-cancer medicament comprises a) a cellular energy inhibitor having the structure according to formula I

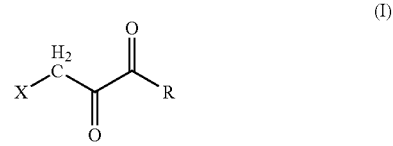
(I)

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl;

b) at least one sugar, which stabilizes the cellular energy inhibitor by substantially preventing the inhibitor from hydrolyzing;

c) a glycolysis inhibitor; and d) a biological buffer that is present in an amount sufficient to at least partially deacidify the cellular energy inhibitor and neutralize metabolic by-products of the cellular energy inhibitor.

In one embodiment, the anti-cancer medicament can be suitable for administration to a subject in a therapeutically effective amount.

In one embodiment, the anti-cancer medicament can be administered to a subject when the subject's blood insulin/glucagon ratio is in the range of about 1 to about 10.

In one embodiment, the anti-cancer medicament can be administered to a subject after fasting for at least 4 hours.

In one embodiment, the anti-cancer medicament can be suitable for administration by a method selected from the group consisting of: inter-arterially, intravenously, inter-peritoneally, inhalation, intra-tumorally, orally, topically, and subcutaneously.

In one embodiment, the administration can be inter-arterially.

In one embodiment, the anti-cancer medicament can be suitable for intra-arterially or intravenously administration for a duration from about 30 minutes to about 8 hours.

In one embodiment, the anti-cancer medicament can be suitable for intra-arterially or intravenously administration for a duration from about 3 hours to about 5 hours.

In one embodiment, the administration can include a regimen lasting from about 1 week to 24 weeks.

In one embodiment, the therapeutically effective amount can include a dosage equivalent to about 1 mM to about 10 mM of the anti-cancer composition in a volume of 25 ml to 1000 ml.

In one embodiment, the cancer can be selected from the group consisting of: childhood fibrolamellar hepatocellular carcinoma (FHCC), hepatocellular carcinoma (HCC), non small cell lung cancer, colon cancer, breast cancer, pancreatic cancer, liver cancer, and combinations thereof.

The following examples illustrate a number of embodiments of the present compositions, systems, and methods that are presently known. However, it is to be understood that the following are only exemplary or illustrative of the application of the principles of the present compositions, systems, and methods. Numerous modifications and alternative compositions, methods, and systems may be devised by those skilled in the art without departing from the spirit and scope of the present systems and methods. The appended claims are intended to cover such modifications and arrangements. Thus, while the present compositions, systems, and methods have been described above with particularity, the following examples provide further detail in connection with what are presently deemed to be the acceptable embodiments.

EXAMPLE

Example 1

Rat Hepatocellular Carcinoma Study

Hepatocellular carcinoma cells were treated with various anti-cancer agents including 3-bromoacetate. FIG. 3 shows a graph of cancer cell viability as a function of µM amounts of the anti-cancer agents over a 23 hour period. As shown in FIG. 3, 3-bromopyruvate provided little cell viability (approx. 5%) with as little as 20 µM used. In fact, 3-bromopyruvate provided 10 times more efficiency as compared to the closest anti-cancer agent, methotrexate, measured in terms of cell viability 5% vs 55%.

Example 2

Lung Cancer Treated with 3-Bromopyruvate

Table 1 provides results of cell proliferation for human lung cancer cells treated with various known anti-cancer agents compared to 3-bromopyruvate.

TABLE 1

| Anticancer Agent at 50 µM, for 24 hrs | Inhibition of Cell Proliferation, % |
|---|---|
| None (control) | 0 |
| 3-Bromopyruvate | 92.5 |
| Carboplatin | 4.5 |
| Cyclophosphamide | 0 |
| Doxorubicin | 39.6 |
| 5-Fluorouracil | 17.8 |
| Methotrexate | 28 |
| Paclitaxel | 0 |

As can be seen from Table 1, for lung cancer cells, 3-bromopyruvate was more than twice as effective as the closest comparative known anti-cancer agent. As such, the present anti-cancer compositions can provide at least a 90% inhibition of cancer cell proliferation.

Example 3

Metastatic Lung Cancer Study

Figure 4A:
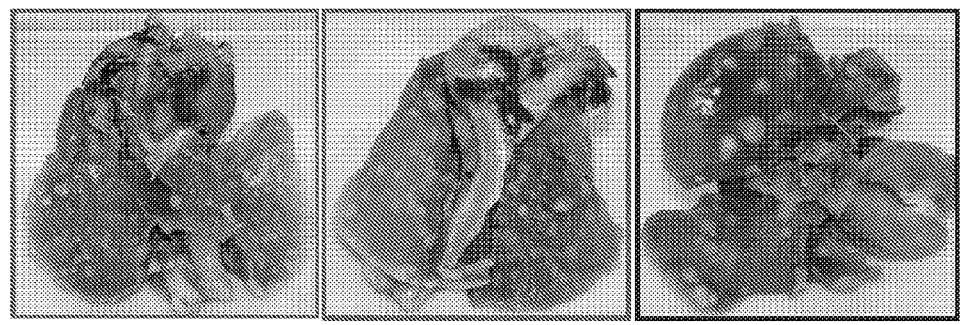
FIGS. 4(*a*) and 4(*b*) show a series of photographs of lungs having metastatic tumors without treatment and with treatment using 3-bromopyruvate, respectively, in accordance with an embodiment of the present invention.
Figure 4B:
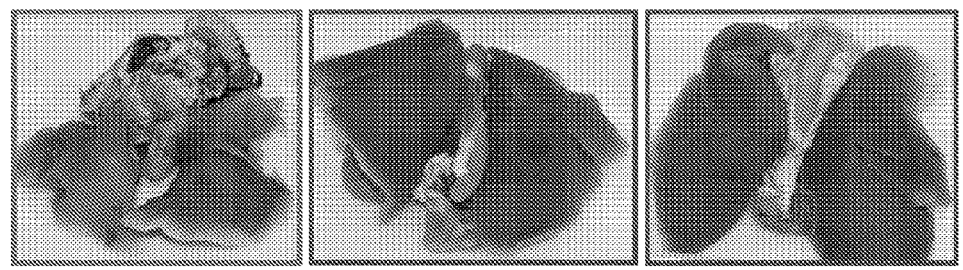

FIG. 4(*a*) shows pictures of dissected lungs of a rabbits having metastatic tumors without the present treatment, while FIG. 4(*b*) shows lungs of a rabbits demonstrating no metastatic lung cancer after treatment using 3-bromoacetate via IP port delivery. As can be seen from FIGS. 4(*a*) and 4(*b*), the present anti-cancer composition was able to prevent metastatic lung tumors.

While the forgoing description and examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. An anti-cancer composition comprising:
 a) a cellular energy inhibitor having the structure according to formula I

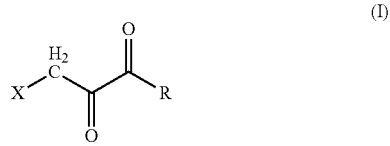

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl;
 b) at least one sugar, which stabilizes the cellular energy inhibitor by substantially inhibiting the inhibitor from hydrolyzing;
 c) a biological buffer that is present in an amount sufficient to at least partially deacidify the cellular energy inhibitor and neutralize metabolic by-products of the cellular energy inhibitor; and
 d) a hexokinase inhibitor;
 wherein the anti-cancer composition treats cancer cells that are positron emission tomography (PET) positive.

2. The anti-cancer composition of claim 1, wherein the hexokinase inhibitor inhibits binding of hexokinase 1 and/or hexokinase 2 to VDAC.

3. The anti-cancer composition of claim 1, wherein the hexokinase inhibitor is an amino acid sequence selected from the group consisting of: SEQ ID NO: 6, SEQ ID NO: 7, SEQ ID NO: 8, SEQ ID NO: 9, and SEQ ID NO. 10.

4. The anti-cancer composition of claim 1, further comprising at least one additive selected from the group consisting of: phospholipids; liposomes; nanoparticles; immune system modulators and/or immune system boosters including brown rice extract, muramyl dipeptide including analogues, mushroom extract, bioflavonoids, Vitamin D3-Binding Protein-Derived Macrophage Activating Factor (GcMAF), inhibitors of nagalase, threonine attached to N-acetylgalactosamine, and antibodies against nagalase; L-lactate dehydrogenase; D-lactate dehydrogenase; nicotinamide adenine dinucleotides; inhibitors for DNA replication; inhibitors for DNA binding; inhibitors for DNA transcription; inhibitors for cell cycle, growth and/or proliferation; inhibitors for signal transduction pathways; inhibitors for angiogensis; small RNAs that interfere with normal gene control including antisense RNA, micro RNA, small hairpin RNA, short hairpin RNA, small interfering RNA; vitamin C; nutritional supplements including vitamins, CoQ10, flavonoids, free fatty acid, alpha lipoic acid, acai, gogi, mango, pomergrante, L-carnitine, selenium; a less biologically active amino acid as compared to its isomer; and mixtures thereof.

5. The anti-cancer composition of claim 1, wherein the cellular energy inhibitor is a 3-halopyruvate selected from the group consisting of: 3-fluoropyruvate, 3-chloropyruvate, 3-bromopyruvate, 3-iodopyruvate, and combinations thereof; in a concentration from about 1.0 mM to about 10.0 mM.

6. The anti-cancer composition of claim 1, wherein the composition comprises a second sugar and a third sugar independently selected from the group consisting of: mannitol, erytritol, isomalt, lactitol, maltitol, sorbitol, xyolitol, dulcitol, ribitol, inositol, and combinations thereof.

7. The anti-cancer composition of claim 6, wherein the sugars are glycerol, inositol, and sorbitol and wherein the composition comprises glycerol in a range from about 0.1 wt % to about 3 wt %, inositol in a range from about 1 wt % to about 5 wt %, and sorbitol in a range from about 30 wt % to about 50 wt %.

8. The anti-cancer composition of claim 1, further comprising d-lactic acid and epinephrine.

9. The anti-cancer composition of claim 1, wherein composition further comprises a glycolysis inhibitor and wherein the glycolysis inhibitor is 2-deoxglucose in a concentration from about 1 mM to about 5 mM.

10. The anti-cancer composition of claim 1, wherein the biological buffer is selected from the group consisting of a citrate buffer, a phosphate buffer, and an acetate buffer.

11. The anti-cancer composition of claim 1, wherein the biological buffer is a citrate buffer.

12. The anti-cancer composition of claim 1, wherein the by-product is a hydrogen halide and the biological buffer is sodium citrate.

13. The anti-cancer composition of claim 12, wherein the hydrogen halide is hydrogen bromide.

14. The anti-cancer composition of claim 1, wherein the composition comprises the biological buffer in a concentration from about 1 mM to about 20 mM.

15. The anti-cancer composition of claim 1, wherein the biological buffer maintains a physiological pH of 5.5 to 8.0.

16. The anti-cancer composition of claim 1, further comprising an antifungal agent and/or antibacterial agent in a concentration from about 0.05 mM to about 0.5 mM.

17. The anti-cancer composition of claim 1, further comprising a mitochondrial inhibitor.

18. The anti-cancer composition of claim 17, wherein the mitochondrial inhibitor is selected from the group consisting of: oligomycin, efrapeptin, aurovertin, and mixtures thereof; in a concentration from about 0.01 mM to about 0.5 mM.

19. A method for the treatment of cancer, comprising administering to a subject the anti-cancer composition of claim 1 in a therapeutically effective amount.

20. The method of claim 19, wherein the administration is selected from the group consisting of: inter-arterially, intra-venously, inter-peritoneally, inhalation, intra-tumorally, orally, topically, and subcutaneously.

21. The method of claim 19, wherein the therapeutically effective amount includes a dosage of about 1 mM to about 10 mM of the anti-cancer composition in a volume of 25 ml to 1000 ml.

22. The method of claim 19, wherein the cancer is selected from the group consisting of: childhood fibrolamellar hepatocellular carcinoma (FHCC), hepatocellular carcinoma (HCC), lung cancer including non small cell lung cancer, colon cancer, pancreatic cancer, liver cancer, breast cancer, cervical cancer, medulloblastoma, neuroblastoma, ovarian cancer, prostate cancer, skin cancer, and combinations thereof.

23. The anti-cancer composition of claim 1, wherein the cancerous cells are in a tissue selected from the group consisting of brain, colon, urogenital, lung, renal, prostate, pancreas, liver, esophagus, stomach, hematopoietic, breast, thymus, testis, ovarian, skin, bone marrow, and uterine.

24. An anti-cancer composition comprising:
a) a cellular energy inhibitor having the structure according to formula I

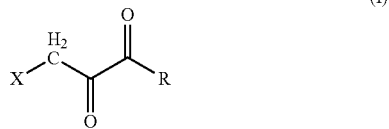

wherein X is selected from the group consisting of: a nitro, an imidazole, a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R" represents H, C1-C6 alkyl, or C6-C12 aryl, and R''' represents H, C1-C20 alkyl or C6-C12 aryl;
b) at least one sugar, which stabilizes the cellular energy inhibitor by substantially inhibiting the inhibitor from hydrolyzing; and
c) a biological buffer that is present in an amount sufficient to at least partially deacidify the cellular energy inhibitor and neutralize metabolic by-products of the cellular energy inhibitor
wherein the anti-cancer composition treats cancer cells that are positron emission tomography (PET) positive.

25. The anti-cancer composition of claim 24, further comprising a glycolysis inhibitor.

26. The anti-cancer composition of claim 25, wherein the glycolysis inhibitor is 2-deoxglucose.

27. The anti-cancer composition of claim 24, wherein the cellular energy inhibitor is a 3-halopyruvate selected from the group consisting of: 3-fluoropyruvate, 3-chloropyruvate, 3-bromopyruvate, 3-iodopyruvate, and combinations thereof.

28. The anti-cancer composition of claim 24, wherein the composition comprises a second sugar and a third sugar independently selected from the group consisting of mannitol, erytritol, isomalt, lactitol, maltitol, sorbitol, xyolitol, dulcitol, ribitol, inositol, and combinations thereof.

29. The anti-cancer composition of claim 28, wherein the sugars are glycerol, inositol, and sorbitol and wherein the composition comprises glycerol in a range from about 0.1 wt % to about 3 wt %, inositol in a range from about 1 wt % to about 5 wt %, and sorbitol in a range from about 30 wt % to about 50 wt %.

30. The anti-cancer composition of claim 24, wherein the composition comprises the biological buffer in a concentration from about 1 mM to about 20 mM and maintains a physiological pH of 5.5 to 8.0.

31. The anti-cancer composition of claim 24, further comprising a halo monocarboxylate compound.

32. The anti-cancer composition of claim 24, further comprising a mitochondrial inhibitor.

* * * * *

SEQUENCE LISTING

```
<160> NUMBER OF SEQ ID NOS: 10

<210> SEQ ID NO 1
<211> LENGTH: 917
<212> TYPE: PRT
<213> ORGANISM: Homo sapiens

<400> SEQUENCE: 1

Met Ile Ala Ala Gln Leu Leu Ala Tyr Tyr Phe Thr Glu Leu Lys Asp
1               5                   10                  15

Asp Gln Val Lys Lys Ile Asp Lys Tyr Leu Tyr Ala Met Arg Leu Ser
            20                  25                  30

Asp Glu Thr Leu Ile Asp Ile Met Thr Arg Phe Arg Lys Glu Met Lys
        35                  40                  45

Asn Gly Leu Ser Arg Asp Phe Asn Pro Thr Ala Thr Val Lys Met Leu
    50                  55                  60
```

```
Pro Thr Phe Val Arg Ser Ile Pro Asp Gly Ser Glu Lys Gly Asp Phe
 65                  70                  75                  80

Ile Ala Leu Asp Leu Gly Gly Ser Ser Phe Arg Ile Leu Arg Val Gln
                 85                  90                  95

Val Asn His Glu Lys Asn Gln Asn Val His Met Glu Ser Glu Val Tyr
                100                 105                 110

Asp Thr Pro Glu Asn Ile Val His Gly Ser Gly Ser Gln Leu Phe Asp
            115                 120                 125

His Val Ala Glu Cys Leu Gly Asp Phe Met Glu Lys Arg Lys Ile Lys
        130                 135                 140

Asp Lys Lys Leu Pro Val Gly Phe Thr Phe Ser Phe Pro Cys Gln Gln
145                 150                 155                 160

Ser Lys Ile Asp Glu Ala Ile Leu Ile Thr Trp Thr Lys Arg Phe Lys
                165                 170                 175

Ala Ser Gly Val Glu Gly Ala Asp Val Val Lys Leu Leu Asn Lys Ala
                180                 185                 190

Ile Lys Lys Arg Gly Asp Tyr Asp Ala Asn Ile Val Ala Val Val Asn
        195                 200                 205

Asp Thr Val Gly Thr Met Met Thr Cys Gly Tyr Asp Asp Gln His Cys
    210                 215                 220

Glu Val Gly Leu Ile Ile Gly Thr Gly Thr Asn Ala Cys Tyr Met Glu
225                 230                 235                 240

Glu Leu Arg His Ile Asp Leu Val Glu Gly Asp Gly Arg Met Cys
                245                 250                 255

Ile Asn Thr Glu Trp Gly Ala Phe Gly Asp Asp Gly Ser Leu Glu Asp
                260                 265                 270

Ile Arg Thr Glu Phe Asp Arg Glu Ile Asp Arg Gly Ser Leu Asn Pro
            275                 280                 285

Gly Lys Gln Leu Phe Glu Lys Met Val Ser Gly Met Tyr Leu Gly Glu
        290                 295                 300

Leu Val Arg Leu Ile Leu Val Lys Met Ala Lys Glu Gly Leu Leu Phe
305                 310                 315                 320

Glu Gly Arg Ile Thr Pro Glu Leu Leu Thr Arg Gly Lys Phe Asn Thr
                325                 330                 335

Ser Asp Val Ser Ala Ile Glu Lys Asn Lys Glu Gly Leu His Asn Ala
                340                 345                 350

Lys Glu Ile Leu Thr Arg Leu Gly Val Glu Pro Ser Asp Asp Asp Cys
        355                 360                 365

Val Ser Val Gln His Val Cys Thr Ile Val Ser Phe Arg Ser Ala Asn
    370                 375                 380

Leu Val Ala Ala Thr Leu Gly Ala Ile Leu Asn Arg Leu Arg Asp Asn
385                 390                 395                 400

Lys Gly Thr Pro Arg Leu Arg Thr Thr Val Gly Val Asp Gly Ser Leu
                405                 410                 415

Tyr Lys Thr His Pro Gln Tyr Ser Arg Arg Phe His Lys Thr Leu Arg
            420                 425                 430

Arg Leu Val Pro Asp Ser Asp Val Arg Phe Leu Leu Ser Glu Ser Gly
        435                 440                 445

Ser Gly Lys Gly Ala Ala Met Val Thr Ala Val Ala Tyr Arg Leu Ala
    450                 455                 460

Glu Gln His Arg Gln Ile Glu Glu Thr Leu Ala His Phe His Leu Thr
465                 470                 475                 480

Lys Asp Met Leu Leu Glu Val Lys Lys Arg Met Arg Ala Glu Met Glu
                485                 490                 495
```

```
Leu Gly Leu Arg Lys Gln Thr His Asn Asn Ala Val Val Lys Met Leu
            500                 505                 510
Pro Ser Phe Val Arg Arg Thr Pro Asp Gly Thr Glu Asn Gly Asp Phe
            515                 520                 525
Leu Ala Leu Asp Leu Gly Gly Thr Asn Phe Arg Val Leu Leu Val Lys
            530                 535                 540
Ile Arg Ser Gly Lys Lys Arg Thr Val Glu Met His Asn Lys Ile Tyr
545                 550                 555                 560
Ala Ile Pro Ile Glu Ile Met Gln Gly Thr Gly Glu Glu Leu Phe Asp
                565                 570                 575
His Ile Val Ser Cys Ile Ser Asp Phe Leu Asp Tyr Met Gly Ile Lys
                580                 585                 590
Gly Pro Arg Met Pro Leu Gly Phe Thr Phe Ser Phe Pro Cys Gln Gln
            595                 600                 605
Thr Ser Leu Asp Ala Gly Ile Leu Ile Thr Trp Thr Lys Gly Phe Lys
            610                 615                 620
Ala Thr Asp Cys Val Gly His Asp Val Val Thr Leu Leu Arg Asp Ala
625                 630                 635                 640
Ile Lys Arg Arg Glu Glu Phe Asp Leu Asp Val Val Ala Val Val Asn
                645                 650                 655
Asp Thr Val Gly Thr Met Met Thr Cys Ala Tyr Glu Glu Pro Thr Cys
            660                 665                 670
Glu Val Gly Leu Ile Val Gly Thr Gly Ser Asn Ala Cys Tyr Met Glu
            675                 680                 685
Glu Met Lys Asn Val Glu Met Val Glu Gly Asp Gln Gly Gln Met Cys
690                 695                 700
Ile Asn Met Glu Trp Gly Ala Phe Gly Asp Asn Gly Cys Leu Asp Asp
705                 710                 715                 720
Ile Arg Thr His Tyr Asp Arg Leu Val Asp Glu Tyr Ser Leu Asn Ala
                725                 730                 735
Gly Lys Gln Arg Tyr Glu Lys Met Ile Ser Gly Met Tyr Leu Gly Glu
            740                 745                 750
Ile Val Arg Asn Ile Leu Ile Asp Phe Thr Lys Lys Gly Phe Leu Phe
            755                 760                 765
Arg Gly Gln Ile Ser Glu Thr Leu Lys Thr Arg Gly Ile Phe Glu Thr
            770                 775                 780
Lys Phe Leu Ser Gln Ile Glu Ser Asp Arg Leu Ala Leu Leu Gln Val
785                 790                 795                 800
Arg Ala Ile Leu Gln Gln Leu Gly Leu Asn Ser Thr Cys Asp Asp Ser
                805                 810                 815
Ile Leu Val Lys Thr Val Cys Gly Val Val Ser Arg Arg Ala Ala Gln
            820                 825                 830
Leu Cys Gly Ala Gly Met Ala Ala Val Val Asp Lys Ile Arg Glu Asn
            835                 840                 845
Arg Gly Leu Asp Arg Leu Asn Val Thr Val Gly Val Asp Gly Thr Leu
            850                 855                 860
Tyr Lys Leu His Pro His Phe Ser Arg Ile Met His Gln Thr Val Lys
865                 870                 875                 880
Glu Leu Ser Pro Lys Cys Asn Val Ser Phe Leu Leu Ser Glu Asp Gly
                885                 890                 895
Ser Gly Lys Gly Ala Ala Leu Ile Thr Ala Val Gly Val Arg Leu Arg
            900                 905                 910
Thr Glu Ala Ser Ser
```

915

<210> SEQ ID NO 2
<211> LENGTH: 916
<212> TYPE: PRT
<213> ORGANISM: Homo sapiens

<400> SEQUENCE: 2

```
Met Asp Cys Glu His Ser Leu Ser Leu Pro Cys Arg Gly Ala Glu Ala
1               5                   10                  15

Trp Glu Ile Gly Ile Asp Lys Tyr Leu Tyr Ala Met Arg Leu Ser Asp
            20                  25                  30

Glu Thr Leu Ile Asp Ile Met Thr Arg Phe Arg Lys Glu Met Lys Asn
        35                  40                  45

Gly Leu Ser Arg Asp Phe Asn Pro Thr Ala Thr Val Lys Met Leu Pro
    50                  55                  60

Thr Phe Val Arg Ser Ile Pro Asp Gly Ser Glu Lys Gly Asp Phe Ile
65                  70                  75                  80

Ala Leu Asp Leu Gly Gly Ser Ser Phe Arg Ile Leu Arg Val Gln Val
                85                  90                  95

Asn His Glu Lys Asn Gln Asn Val His Met Glu Ser Glu Val Tyr Asp
            100                 105                 110

Thr Pro Glu Asn Ile Val His Gly Ser Gly Ser Gln Leu Phe Asp His
        115                 120                 125

Val Ala Glu Cys Leu Gly Asp Phe Met Glu Lys Arg Lys Ile Lys Asp
    130                 135                 140

Lys Lys Leu Pro Val Gly Phe Thr Phe Ser Phe Pro Cys Gln Gln Ser
145                 150                 155                 160

Lys Ile Asp Glu Ala Ile Leu Ile Thr Trp Thr Lys Arg Phe Lys Ala
                165                 170                 175

Ser Gly Val Glu Gly Ala Asp Val Val Lys Leu Leu Asn Lys Ala Ile
            180                 185                 190

Lys Lys Arg Gly Asp Tyr Asp Ala Asn Ile Val Ala Val Val Asn Asp
        195                 200                 205

Thr Val Gly Thr Met Met Thr Cys Gly Tyr Asp Asp Gln His Cys Glu
    210                 215                 220

Val Gly Leu Ile Ile Gly Thr Gly Thr Asn Ala Cys Tyr Met Glu Glu
225                 230                 235                 240

Leu Arg His Ile Asp Leu Val Glu Gly Asp Glu Gly Arg Met Cys Ile
                245                 250                 255

Asn Thr Glu Trp Gly Ala Phe Gly Asp Asp Gly Ser Leu Glu Asp Ile
            260                 265                 270

Arg Thr Glu Phe Asp Arg Glu Ile Asp Arg Gly Ser Leu Asn Pro Gly
        275                 280                 285

Lys Gln Leu Phe Glu Lys Met Val Ser Gly Met Tyr Leu Gly Glu Leu
    290                 295                 300

Val Arg Leu Ile Leu Val Lys Met Ala Lys Glu Gly Leu Leu Phe Glu
305                 310                 315                 320

Gly Arg Ile Thr Pro Glu Leu Leu Thr Arg Gly Lys Phe Asn Thr Ser
                325                 330                 335

Asp Val Ser Ala Ile Glu Lys Asn Lys Glu Gly Leu His Asn Ala Lys
            340                 345                 350

Glu Ile Leu Thr Arg Leu Gly Val Glu Pro Ser Asp Asp Cys Val
        355                 360                 365

Ser Val Gln His Val Cys Thr Ile Val Ser Phe Arg Ser Ala Asn Leu
```

```
                370             375             380
Val Ala Ala Thr Leu Gly Ala Ile Leu Asn Arg Leu Arg Asp Asn Lys
385                 390                 395                 400

Gly Thr Pro Arg Leu Arg Thr Thr Val Gly Val Asp Gly Ser Leu Tyr
                405                 410                 415

Lys Thr His Pro Gln Tyr Ser Arg Arg Phe His Lys Thr Leu Arg Arg
                420                 425                 430

Leu Val Pro Asp Ser Asp Val Arg Phe Leu Leu Ser Glu Ser Gly Ser
                435                 440                 445

Gly Lys Gly Ala Ala Met Val Thr Ala Val Ala Tyr Arg Leu Ala Glu
                450                 455                 460

Gln His Arg Gln Ile Glu Glu Thr Leu Ala His Phe His Leu Thr Lys
465                 470                 475                 480

Asp Met Leu Leu Glu Val Lys Lys Arg Met Arg Ala Glu Met Glu Leu
                485                 490                 495

Gly Leu Arg Lys Gln Thr His Asn Asn Ala Val Val Lys Met Leu Pro
                500                 505                 510

Ser Phe Val Arg Arg Thr Pro Asp Gly Thr Glu Asn Gly Asp Phe Leu
                515                 520                 525

Ala Leu Asp Leu Gly Gly Thr Asn Phe Arg Val Leu Leu Val Lys Ile
530                 535                 540

Arg Ser Gly Lys Lys Arg Thr Val Glu Met His Asn Lys Ile Tyr Ala
545                 550                 555                 560

Ile Pro Ile Glu Ile Met Gln Gly Thr Gly Glu Glu Leu Phe Asp His
                565                 570                 575

Ile Val Ser Cys Ile Ser Asp Phe Leu Asp Tyr Met Gly Ile Lys Gly
                580                 585                 590

Pro Arg Met Pro Leu Gly Phe Thr Phe Ser Phe Pro Cys Gln Gln Thr
                595                 600                 605

Ser Leu Asp Ala Gly Ile Leu Ile Thr Trp Thr Lys Gly Phe Lys Ala
                610                 615                 620

Thr Asp Cys Val Gly His Asp Val Val Thr Leu Leu Arg Asp Ala Ile
625                 630                 635                 640

Lys Arg Arg Glu Glu Phe Asp Leu Asp Val Val Ala Val Val Asn Asp
                645                 650                 655

Thr Val Gly Thr Met Met Thr Cys Ala Tyr Glu Glu Pro Thr Cys Glu
                660                 665                 670

Val Gly Leu Ile Val Gly Thr Gly Ser Asn Ala Cys Tyr Met Glu Glu
                675                 680                 685

Met Lys Asn Val Glu Met Val Glu Gly Asp Gln Gly Gln Met Cys Ile
690                 695                 700

Asn Met Glu Trp Gly Ala Phe Gly Asp Asn Gly Cys Leu Asp Asp Ile
705                 710                 715                 720

Arg Thr His Tyr Asp Arg Leu Val Asp Glu Tyr Ser Leu Asn Ala Gly
                725                 730                 735

Lys Gln Arg Tyr Glu Lys Met Ile Ser Gly Met Tyr Leu Gly Glu Ile
                740                 745                 750

Val Arg Asn Ile Leu Ile Asp Phe Thr Lys Lys Gly Phe Leu Phe Arg
                755                 760                 765

Gly Gln Ile Ser Glu Thr Leu Lys Thr Arg Gly Ile Phe Glu Thr Lys
                770                 775                 780

Phe Leu Ser Gln Ile Glu Ser Asp Arg Leu Ala Leu Leu Gln Val Arg
785                 790                 795                 800
```

```
Ala Ile Leu Gln Gln Leu Gly Leu Asn Ser Thr Cys Asp Asp Ser Ile
            805                 810                 815

Leu Val Lys Thr Val Cys Gly Val Val Ser Arg Arg Ala Ala Gln Leu
            820                 825                 830

Cys Gly Ala Gly Met Ala Ala Val Val Asp Lys Ile Arg Glu Asn Arg
            835                 840                 845

Gly Leu Asp Arg Leu Asn Val Thr Val Gly Val Asp Gly Thr Leu Tyr
            850                 855                 860

Lys Leu His Pro His Phe Ser Arg Ile Met His Gln Thr Val Lys Glu
865                 870                 875                 880

Leu Ser Pro Lys Cys Asn Val Ser Phe Leu Ser Glu Asp Gly Ser
            885                 890                 895

Gly Lys Gly Ala Ala Leu Ile Thr Ala Val Gly Val Arg Leu Arg Thr
            900                 905                 910

Glu Ala Ser Ser
            915

<210> SEQ ID NO 3
<211> LENGTH: 921
<212> TYPE: PRT
<213> ORGANISM: Homo sapiens

<400> SEQUENCE: 3

Met Gly Gln Ile Cys Gln Arg Glu Ser Ala Thr Ala Ala Glu Lys Pro
1               5                   10                  15

Lys Leu His Leu Leu Ala Glu Ser Glu Ile Asp Lys Tyr Leu Tyr Ala
            20                  25                  30

Met Arg Leu Ser Asp Glu Thr Leu Ile Asp Ile Met Thr Arg Phe Arg
            35                  40                  45

Lys Glu Met Lys Asn Gly Leu Ser Arg Asp Phe Asn Pro Thr Ala Thr
        50                  55                  60

Val Lys Met Leu Pro Thr Phe Val Arg Ser Ile Pro Asp Gly Ser Glu
65                  70                  75                  80

Lys Gly Asp Phe Ile Ala Leu Asp Leu Gly Gly Ser Ser Phe Arg Ile
            85                  90                  95

Leu Arg Val Gln Val Asn His Glu Lys Asn Gln Asn Val His Met Glu
            100                 105                 110

Ser Glu Val Tyr Asp Thr Pro Glu Asn Ile Val His Gly Ser Gly Ser
            115                 120                 125

Gln Leu Phe Asp His Val Ala Glu Cys Leu Gly Asp Phe Met Glu Lys
        130                 135                 140

Arg Lys Ile Lys Asp Lys Lys Leu Pro Val Gly Phe Thr Phe Ser Phe
145                 150                 155                 160

Pro Cys Gln Gln Ser Lys Ile Asp Glu Ala Ile Leu Ile Thr Trp Thr
            165                 170                 175

Lys Arg Phe Lys Ala Ser Gly Val Glu Gly Ala Asp Val Val Lys Leu
            180                 185                 190

Leu Asn Lys Ala Ile Lys Lys Arg Gly Asp Tyr Asp Ala Asn Ile Val
            195                 200                 205

Ala Val Val Asn Asp Thr Val Gly Thr Met Met Thr Cys Gly Tyr Asp
        210                 215                 220

Asp Gln His Cys Glu Val Gly Leu Ile Ile Gly Thr Gly Thr Asn Ala
225                 230                 235                 240

Cys Tyr Met Glu Glu Leu Arg His Ile Asp Leu Val Glu Gly Asp Glu
            245                 250                 255
```

-continued

```
Gly Arg Met Cys Ile Asn Thr Glu Trp Gly Ala Phe Gly Asp Asp Gly
            260                 265                 270

Ser Leu Glu Asp Ile Arg Thr Glu Phe Asp Arg Glu Ile Asp Arg Gly
            275                 280                 285

Ser Leu Asn Pro Gly Lys Gln Leu Phe Glu Lys Met Val Ser Gly Met
            290                 295                 300

Tyr Leu Gly Glu Leu Val Arg Leu Ile Leu Val Lys Met Ala Lys Glu
305                 310                 315                 320

Gly Leu Leu Phe Glu Gly Arg Ile Thr Pro Glu Leu Leu Thr Arg Gly
                325                 330                 335

Lys Phe Asn Thr Ser Asp Val Ser Ala Ile Glu Lys Asn Lys Glu Gly
            340                 345                 350

Leu His Asn Ala Lys Glu Ile Leu Thr Arg Leu Gly Val Glu Pro Ser
            355                 360                 365

Asp Asp Asp Cys Val Ser Val Gln His Val Cys Thr Ile Val Ser Phe
            370                 375                 380

Arg Ser Ala Asn Leu Val Ala Ala Thr Leu Gly Ala Ile Leu Asn Arg
385                 390                 395                 400

Leu Arg Asp Asn Lys Gly Thr Pro Arg Leu Arg Thr Thr Val Gly Val
                405                 410                 415

Asp Gly Ser Leu Tyr Lys Thr His Pro Gln Tyr Ser Arg Arg Phe His
            420                 425                 430

Lys Thr Leu Arg Arg Leu Val Pro Asp Ser Asp Val Arg Phe Leu Leu
            435                 440                 445

Ser Glu Ser Gly Ser Gly Lys Gly Ala Ala Met Val Thr Ala Val Ala
            450                 455                 460

Tyr Arg Leu Ala Glu Gln His Arg Gln Ile Glu Glu Thr Leu Ala His
465                 470                 475                 480

Phe His Leu Thr Lys Asp Met Leu Leu Glu Val Lys Lys Arg Met Arg
                485                 490                 495

Ala Glu Met Glu Leu Gly Leu Arg Lys Gln Thr His Asn Asn Ala Val
            500                 505                 510

Val Lys Met Leu Pro Ser Phe Val Arg Arg Thr Pro Asp Gly Thr Glu
            515                 520                 525

Asn Gly Asp Phe Leu Ala Leu Asp Leu Gly Gly Thr Asn Phe Arg Val
            530                 535                 540

Leu Leu Val Lys Ile Arg Ser Gly Lys Lys Arg Thr Val Glu Met His
545                 550                 555                 560

Asn Lys Ile Tyr Ala Ile Pro Ile Glu Ile Met Gln Gly Thr Gly Glu
                565                 570                 575

Glu Leu Phe Asp His Ile Val Ser Cys Ile Ser Asp Phe Leu Asp Tyr
            580                 585                 590

Met Gly Ile Lys Gly Pro Arg Met Pro Leu Gly Phe Thr Phe Ser Phe
            595                 600                 605

Pro Cys Gln Gln Thr Ser Leu Asp Ala Gly Ile Leu Ile Thr Trp Thr
            610                 615                 620

Lys Gly Phe Lys Ala Thr Asp Cys Val Gly His Asp Val Thr Leu Leu
625                 630                 635                 640

Leu Arg Asp Ala Ile Lys Arg Arg Glu Glu Phe Asp Leu Asp Val Val
                645                 650                 655

Ala Val Val Asn Asp Thr Val Gly Thr Met Met Thr Cys Ala Tyr Glu
            660                 665                 670

Glu Pro Thr Cys Glu Val Gly Leu Ile Val Gly Thr Gly Ser Asn Ala
            675                 680                 685
```

Cys Tyr Met Glu Glu Met Lys Asn Val Glu Met Val Glu Gly Asp Gln
            690                 695                 700

Gly Gln Met Cys Ile Asn Met Glu Trp Gly Ala Phe Gly Asp Asn Gly
705                 710                 715                 720

Cys Leu Asp Asp Ile Arg Thr His Tyr Asp Arg Leu Val Asp Glu Tyr
            725                 730                 735

Ser Leu Asn Ala Gly Lys Gln Arg Tyr Glu Lys Met Ile Ser Gly Met
            740                 745                 750

Tyr Leu Gly Glu Ile Val Arg Asn Ile Leu Ile Asp Phe Thr Lys Lys
            755                 760                 765

Gly Phe Leu Phe Arg Gly Gln Ile Ser Glu Thr Leu Lys Thr Arg Gly
            770                 775                 780

Ile Phe Glu Thr Lys Phe Leu Ser Gln Ile Glu Ser Asp Arg Leu Ala
785                 790                 795                 800

Leu Leu Gln Val Arg Ala Ile Leu Gln Gln Leu Gly Leu Asn Ser Thr
            805                 810                 815

Cys Asp Asp Ser Ile Leu Val Lys Thr Val Cys Gly Val Val Ser Arg
            820                 825                 830

Arg Ala Ala Gln Leu Cys Gly Ala Gly Met Ala Ala Val Val Asp Lys
            835                 840                 845

Ile Arg Glu Asn Arg Gly Leu Asp Arg Leu Asn Val Thr Val Gly Val
850                 855                 860

Asp Gly Thr Leu Tyr Lys Leu His Pro His Phe Ser Arg Ile Met His
865                 870                 875                 880

Gln Thr Val Lys Glu Leu Ser Pro Lys Cys Asn Val Ser Phe Leu Leu
            885                 890                 895

Ser Glu Asp Gly Ser Gly Lys Gly Ala Ala Leu Ile Thr Ala Val Gly
            900                 905                 910

Val Arg Leu Arg Thr Glu Ala Ser Ser
            915                 920

<210> SEQ ID NO 4
<211> LENGTH: 905
<212> TYPE: PRT
<213> ORGANISM: Homo sapiens

<400> SEQUENCE: 4

Met Ala Lys Arg Ala Leu Arg Asp Phe Ile Asp Lys Tyr Leu Tyr Ala
1               5                   10                  15

Met Arg Leu Ser Asp Glu Thr Leu Ile Asp Ile Met Thr Arg Phe Arg
            20                  25                  30

Lys Glu Met Lys Asn Gly Leu Ser Arg Asp Phe Asn Pro Thr Ala Thr
            35                  40                  45

Val Lys Met Leu Pro Thr Phe Val Arg Ser Ile Pro Asp Gly Ser Glu
50                  55                  60

Lys Gly Asp Phe Ile Ala Leu Asp Leu Gly Gly Ser Ser Phe Arg Ile
65                  70                  75                  80

Leu Arg Val Gln Val Asn His Glu Lys Asn Gln Asn Val His Met Glu
            85                  90                  95

Ser Glu Val Tyr Asp Thr Pro Glu Asn Ile Val His Gly Ser Gly Ser
            100                 105                 110

Gln Leu Phe Asp His Val Ala Glu Cys Leu Gly Asp Phe Met Glu Lys
            115                 120                 125

Arg Lys Ile Lys Asp Lys Lys Leu Pro Val Gly Phe Thr Phe Ser Phe
130                 135                 140

-continued

```
Pro Cys Gln Gln Ser Lys Ile Asp Glu Ala Ile Leu Ile Thr Trp Thr
145                 150                 155                 160

Lys Arg Phe Lys Ala Ser Gly Val Glu Gly Ala Asp Val Val Lys Leu
            165                 170                 175

Leu Asn Lys Ala Ile Lys Lys Arg Gly Asp Tyr Asp Ala Asn Ile Val
        180                 185                 190

Ala Val Val Asn Asp Thr Val Gly Thr Met Met Thr Cys Gly Tyr Asp
    195                 200                 205

Asp Gln His Cys Glu Val Gly Leu Ile Ile Gly Thr Gly Thr Asn Ala
210                 215                 220

Cys Tyr Met Glu Glu Leu Arg His Ile Asp Leu Val Glu Gly Asp Glu
225                 230                 235                 240

Gly Arg Met Cys Ile Asn Thr Glu Trp Gly Ala Phe Gly Asp Asp Gly
                245                 250                 255

Ser Leu Glu Asp Ile Arg Thr Glu Phe Asp Arg Glu Ile Asp Arg Gly
            260                 265                 270

Ser Leu Asn Pro Gly Lys Gln Leu Phe Glu Lys Met Val Ser Gly Met
        275                 280                 285

Tyr Leu Gly Glu Leu Val Arg Leu Ile Leu Val Lys Met Ala Lys Glu
290                 295                 300

Gly Leu Leu Phe Glu Gly Arg Ile Thr Pro Glu Leu Leu Thr Arg Gly
305                 310                 315                 320

Lys Phe Asn Thr Ser Asp Val Ser Ala Ile Glu Lys Asn Lys Glu Gly
                325                 330                 335

Leu His Asn Ala Lys Glu Ile Leu Thr Arg Leu Gly Val Glu Pro Ser
            340                 345                 350

Asp Asp Asp Cys Val Ser Val Gln His Val Cys Thr Ile Val Ser Phe
        355                 360                 365

Arg Ser Ala Asn Leu Val Ala Ala Thr Leu Gly Ala Ile Leu Asn Arg
370                 375                 380

Leu Arg Asp Asn Lys Gly Thr Pro Arg Leu Arg Thr Thr Val Gly Val
385                 390                 395                 400

Asp Gly Ser Leu Tyr Lys Thr His Pro Gln Tyr Ser Arg Arg Phe His
                405                 410                 415

Lys Thr Leu Arg Arg Leu Val Pro Asp Ser Asp Val Arg Phe Leu Leu
            420                 425                 430

Ser Glu Ser Gly Ser Gly Lys Gly Ala Ala Met Val Thr Ala Val Ala
        435                 440                 445

Tyr Arg Leu Ala Glu Gln His Arg Gln Ile Glu Glu Thr Leu Ala His
450                 455                 460

Phe His Leu Thr Lys Asp Met Leu Leu Glu Val Lys Lys Arg Met Arg
465                 470                 475                 480

Ala Glu Met Glu Leu Gly Leu Arg Lys Gln Thr His Asn Asn Ala Val
                485                 490                 495

Val Lys Met Leu Pro Ser Phe Val Arg Arg Thr Pro Asp Gly Thr Glu
            500                 505                 510

Asn Gly Asp Phe Leu Ala Leu Asp Leu Gly Gly Thr Asn Phe Arg Val
        515                 520                 525

Leu Leu Val Lys Ile Arg Ser Gly Lys Lys Arg Thr Val Glu Met His
        530                 535                 540

Asn Lys Ile Tyr Ala Ile Pro Ile Glu Ile Met Gln Gly Thr Gly Glu
545                 550                 555                 560

Glu Leu Phe Asp His Ile Val Ser Cys Ile Ser Asp Phe Leu Asp Tyr
```

```
                  565                 570                 575
Met Gly Ile Lys Gly Pro Arg Met Pro Leu Gly Phe Thr Phe Ser Phe
                580                 585                 590

Pro Cys Gln Gln Thr Ser Leu Asp Ala Gly Ile Leu Ile Thr Trp Thr
                595                 600                 605

Lys Gly Phe Lys Ala Thr Asp Cys Val Gly His Asp Val Val Thr Leu
                610                 615                 620

Leu Arg Asp Ala Ile Lys Arg Glu Glu Phe Asp Leu Asp Val Val
625                 630                 635                 640

Ala Val Val Asn Asp Thr Val Gly Thr Met Met Thr Cys Ala Tyr Glu
                645                 650                 655

Glu Pro Thr Cys Glu Val Gly Leu Ile Val Gly Thr Gly Ser Asn Ala
                660                 665                 670

Cys Tyr Met Glu Glu Met Lys Asn Val Glu Met Val Glu Gly Asp Gln
                675                 680                 685

Gly Gln Met Cys Ile Asn Met Glu Trp Gly Ala Phe Gly Asp Asn Gly
                690                 695                 700

Cys Leu Asp Asp Ile Arg Thr His Tyr Asp Arg Leu Val Asp Glu Tyr
705                 710                 715                 720

Ser Leu Asn Ala Gly Lys Gln Arg Tyr Glu Lys Met Ile Ser Gly Met
                725                 730                 735

Tyr Leu Gly Glu Ile Val Arg Asn Ile Leu Ile Asp Phe Thr Lys Lys
                740                 745                 750

Gly Phe Leu Phe Arg Gly Gln Ile Ser Glu Thr Leu Lys Thr Arg Gly
                755                 760                 765

Ile Phe Glu Thr Lys Phe Leu Ser Gln Ile Glu Ser Asp Arg Leu Ala
                770                 775                 780

Leu Leu Gln Val Arg Ala Ile Leu Gln Gln Leu Gly Leu Asn Ser Thr
785                 790                 795                 800

Cys Asp Asp Ser Ile Leu Val Lys Thr Val Cys Gly Val Val Ser Arg
                805                 810                 815

Arg Ala Ala Gln Leu Cys Gly Ala Gly Met Ala Ala Val Val Asp Lys
                820                 825                 830

Ile Arg Glu Asn Arg Gly Leu Asp Arg Leu Asn Val Thr Val Gly Val
                835                 840                 845

Asp Gly Thr Leu Tyr Lys Leu His Pro His Phe Ser Arg Ile Met His
                850                 855                 860

Gln Thr Val Lys Glu Leu Ser Pro Lys Cys Asn Val Ser Phe Leu Leu
865                 870                 875                 880

Ser Glu Asp Gly Ser Gly Lys Gly Ala Ala Leu Ile Thr Ala Val Gly
                885                 890                 895

Val Arg Leu Arg Thr Glu Ala Ser Ser
                900                 905

<210> SEQ ID NO 5
<211> LENGTH: 917
<212> TYPE: PRT
<213> ORGANISM: Homo sapiens

<400> SEQUENCE: 5

Met Ile Ala Ser His Leu Leu Ala Tyr Phe Phe Thr Glu Leu Asn His
1               5                   10                  15

Asp Gln Val Gln Lys Val Asp Gln Tyr Leu Tyr His Met Arg Leu Ser
                20                  25                  30

Asp Glu Thr Leu Leu Glu Ile Ser Lys Arg Phe Arg Lys Glu Met Glu
```

```
              35                  40                  45
Lys Gly Leu Gly Ala Thr Thr His Pro Thr Ala Val Lys Met Leu
         50                  55                  60

Pro Thr Phe Val Arg Ser Thr Pro Asp Gly Thr Glu His Gly Glu Phe
 65                  70                  75                  80

Leu Ala Leu Asp Leu Gly Gly Thr Asn Phe Arg Val Leu Trp Val Lys
                 85                  90                  95

Val Thr Asp Asn Gly Leu Gln Lys Val Glu Met Glu Asn Gln Ile Tyr
                100                 105                 110

Ala Ile Pro Glu Asp Ile Met Arg Gly Ser Gly Thr Gln Leu Phe Asp
                115                 120                 125

His Ile Ala Glu Cys Leu Ala Asn Phe Met Asp Lys Leu Gln Ile Lys
                130                 135                 140

Asp Lys Lys Leu Pro Leu Gly Phe Thr Phe Ser Phe Pro Cys His Gln
145                 150                 155                 160

Thr Lys Leu Asp Glu Ser Phe Leu Val Ser Trp Thr Lys Gly Phe Lys
                165                 170                 175

Ser Ser Gly Val Glu Gly Arg Asp Val Val Ala Leu Ile Arg Lys Ala
                180                 185                 190

Ile Gln Arg Arg Gly Asp Phe Asp Ile Asp Ile Val Ala Val Val Asn
                195                 200                 205

Asp Thr Val Gly Thr Met Met Thr Cys Gly Tyr Asp Asp His Asn Cys
210                 215                 220

Glu Ile Gly Leu Ile Val Gly Thr Gly Ser Asn Ala Cys Tyr Met Glu
225                 230                 235                 240

Glu Met Arg His Ile Asp Met Val Glu Gly Asp Glu Gly Arg Met Cys
                245                 250                 255

Ile Asn Met Glu Trp Gly Ala Phe Gly Asp Asp Gly Ser Leu Asn Asp
                260                 265                 270

Ile Arg Thr Glu Phe Asp Gln Glu Ile Asp Met Gly Ser Leu Asn Pro
                275                 280                 285

Gly Lys Gln Leu Phe Glu Lys Met Ile Ser Gly Met Tyr Met Gly Glu
                290                 295                 300

Leu Val Arg Leu Ile Leu Val Lys Met Ala Lys Glu Glu Leu Leu Phe
305                 310                 315                 320

Gly Gly Lys Leu Ser Pro Glu Leu Leu Asn Thr Gly Arg Phe Glu Thr
                325                 330                 335

Lys Asp Ile Ser Asp Ile Glu Gly Glu Lys Asp Gly Ile Arg Lys Ala
                340                 345                 350

Arg Glu Val Leu Met Arg Leu Gly Leu Asp Pro Thr Gln Glu Asp Cys
                355                 360                 365

Val Ala Thr His Arg Ile Cys Gln Ile Val Ser Thr Arg Ser Ala Ser
                370                 375                 380

Leu Cys Ala Ala Thr Leu Ala Ala Val Leu Gln Arg Ile Lys Glu Asn
385                 390                 395                 400

Lys Gly Glu Glu Arg Leu Arg Ser Thr Ile Gly Val Asp Gly Ser Val
                405                 410                 415

Tyr Lys Lys His Pro His Phe Ala Lys Arg Leu His Lys Thr Val Arg
                420                 425                 430

Arg Leu Val Pro Gly Cys Asp Val Arg Phe Leu Arg Ser Glu Asp Gly
                435                 440                 445

Ser Gly Lys Gly Ala Ala Met Val Thr Ala Val Ala Tyr Arg Leu Ala
450                 455                 460
```

```
Asp Gln His Arg Ala Arg Gln Lys Thr Leu Glu His Leu Gln Leu Ser
465                 470                 475                 480

His Asp Gln Leu Leu Glu Val Lys Arg Arg Met Lys Val Glu Met Glu
            485                 490                 495

Arg Gly Leu Ser Lys Glu Thr His Ala Ser Ala Pro Val Lys Met Leu
        500                 505                 510

Pro Thr Tyr Val Cys Ala Thr Pro Asp Gly Thr Glu Lys Gly Asp Phe
    515                 520                 525

Leu Ala Leu Asp Leu Gly Gly Thr Asn Phe Arg Val Leu Leu Val Arg
530                 535                 540

Val Arg Asn Gly Lys Trp Gly Val Glu Met His Asn Lys Ile Tyr
545                 550                 555                 560

Ala Ile Pro Gln Glu Val Met His Gly Thr Gly Asp Glu Leu Phe Asp
            565                 570                 575

His Ile Val Gln Cys Ile Ala Asp Phe Leu Glu Tyr Met Gly Met Lys
            580                 585                 590

Gly Val Ser Leu Pro Leu Gly Phe Thr Phe Ser Phe Pro Cys Gln Gln
        595                 600                 605

Asn Ser Leu Asp Glu Ser Ile Leu Leu Lys Trp Thr Lys Gly Phe Lys
610                 615                 620

Ala Ser Gly Cys Glu Gly Glu Asp Val Val Thr Leu Leu Lys Glu Ala
625                 630                 635                 640

Ile His Arg Arg Glu Glu Phe Asp Leu Asp Val Val Ala Val Val Asn
                645                 650                 655

Asp Thr Val Gly Thr Met Met Thr Cys Gly Phe Glu Asp Pro His Cys
            660                 665                 670

Glu Val Gly Leu Ile Val Gly Thr Gly Ser Asn Ala Cys Tyr Met Glu
        675                 680                 685

Glu Met Arg Asn Val Glu Leu Val Glu Gly Glu Gly Arg Met Cys
        690                 695                 700

Val Asn Met Glu Trp Gly Ala Phe Gly Asp Asn Gly Cys Leu Asp Asp
705                 710                 715                 720

Phe Arg Thr Glu Phe Asp Val Ala Val Asp Glu Leu Ser Leu Asn Pro
                725                 730                 735

Gly Lys Gln Arg Phe Glu Lys Met Ile Ser Gly Met Tyr Leu Gly Glu
            740                 745                 750

Ile Val Arg Asn Ile Leu Ile Asp Phe Thr Lys Arg Gly Leu Leu Phe
        755                 760                 765

Arg Gly Arg Ile Ser Glu Arg Leu Lys Thr Arg Gly Ile Phe Glu Thr
770                 775                 780

Lys Phe Leu Ser Gln Ile Glu Ser Asp Cys Leu Ala Leu Leu Gln Val
785                 790                 795                 800

Arg Ala Ile Leu Gln His Leu Gly Leu Glu Ser Thr Cys Asp Asp Ser
                805                 810                 815

Ile Ile Val Lys Glu Val Cys Thr Val Val Ala Arg Arg Ala Ala Gln
            820                 825                 830

Leu Cys Gly Ala Gly Met Ala Ala Val Val Asp Arg Ile Arg Glu Asn
        835                 840                 845

Arg Gly Leu Asp Ala Leu Lys Val Thr Val Gly Val Asp Gly Thr Leu
        850                 855                 860

Tyr Lys Leu His Pro His Phe Ala Lys Val Met His Glu Thr Val Lys
865                 870                 875                 880

Asp Leu Ala Pro Lys Cys Asp Val Ser Phe Leu Gln Ser Glu Asp Gly
                885                 890                 895
```

Ser Gly Lys Gly Ala Ala Leu Ile Thr Ala Val Ala Cys Arg Ile Arg
            900                 905                 910

Glu Ala Gly Gln Arg
        915

<210> SEQ ID NO 6
<211> LENGTH: 25
<212> TYPE: PRT
<213> ORGANISM: Homo sapiens

<400> SEQUENCE: 6

Met Ile Ala Ala Gln Leu Leu Ala Tyr Tyr Phe Thr Glu Leu Lys Asp
1               5                   10                  15

Asp Gln Val Lys Lys Ile Asp Lys Tyr
            20                  25

<210> SEQ ID NO 7
<211> LENGTH: 25
<212> TYPE: PRT
<213> ORGANISM: Homo sapiens

<400> SEQUENCE: 7

Met Asp Cys Glu His Ser Leu Ser Leu Pro Cys Arg Gly Ala Glu Ala
1               5                   10                  15

Trp Glu Ile Gly Ile Asp Lys Tyr Leu
            20                  25

<210> SEQ ID NO 8
<211> LENGTH: 25
<212> TYPE: PRT
<213> ORGANISM: Homo sapiens

<400> SEQUENCE: 8

Met Gly Gln Ile Cys Gln Arg Glu Ser Ala Thr Ala Ala Glu Lys Pro
1               5                   10                  15

Lys Leu His Leu Leu Ala Glu Ser Glu
            20                  25

<210> SEQ ID NO 9
<211> LENGTH: 25
<212> TYPE: PRT
<213> ORGANISM: Homo sapiens

<400> SEQUENCE: 9

Met Ala Lys Arg Ala Leu Arg Asp Phe Ile Asp Lys Tyr Leu Tyr Ala
1               5                   10                  15

Met Arg Leu Ser Asp Glu Thr Leu Ile
            20                  25

<210> SEQ ID NO 10
<211> LENGTH: 25
<212> TYPE: PRT
<213> ORGANISM: Homo sapiens

<400> SEQUENCE: 10

Met Ile Ala Ser His Leu Leu Ala Tyr Phe Phe Thr Glu Leu Asn His
1               5                   10                  15

Asp Gln Val Gln Lys Val Asp Gln Tyr
            20                  25